(12) United States Patent
Herekar et al.

(10) Patent No.: US 11,369,516 B2
(45) Date of Patent: Jun. 28, 2022

(54) SCLERAL TRANSLOCATION ELASTO-MODULATION METHODS AND APPARATUS

(71) Applicant: ALeyeGN Technologies LLC, Saratoga, CA (US)

(72) Inventors: Satish Herekar, Palo Alto, CA (US); Rajeev Herekar, San Diego, CA (US)

(73) Assignee: ALeyeGN Technologies LLC, Saratoga, CA (US)

( * ) Notice: Subject to any disclaimer, the term of this patent is extended or adjusted under 35 U.S.C. 154(b) by 110 days.

(21) Appl. No.: 16/551,475

(22) Filed: Aug. 26, 2019

(65) Prior Publication Data
US 2020/0000634 A1 Jan. 2, 2020

Related U.S. Application Data

(63) Continuation of application No. 14/854,390, filed on Sep. 15, 2015, now abandoned, which is a
(Continued)

(51) Int. Cl.
*A61F 9/008* (2006.01)

(52) U.S. Cl.
CPC .......... *A61F 9/00821* (2013.01); *A61F 9/008* (2013.01); *A61F 2009/00865* (2013.01);
(Continued)

(58) Field of Classification Search
CPC .................. A61F 9/00821; A61F 9/008; A61F 2009/00865; A61F 2009/00895; A61F 2009/00868
See application file for complete search history.

(56) References Cited

U.S. PATENT DOCUMENTS

| 4,565,197 A | 1/1986 | Daly |
| 5,529,076 A | 6/1996 | Schachar |

(Continued)

FOREIGN PATENT DOCUMENTS

| AU | 2004200303 | 2/2004 |
| AU | 2007202052 | 5/2007 |

(Continued)

OTHER PUBLICATIONS

"Mission for Vision USA : Anatomy of the Human Eye", (Jul. 10, 2010), p. 1, URL: http://www.images.missionforvisionusa.org/anatomy/2005/10/ciliary-body-histology-answers.ht ml, XP055295916.
(Continued)

*Primary Examiner* — Gary Jackson
*Assistant Examiner* — Zahed Kabir
(74) *Attorney, Agent, or Firm* — FisherBroyles LLP; John Shimmick

(57) ABSTRACT

A laser delivery system is configured to delivery light energy to soften and realign the tissue of the eye in order to increase accommodation and treat glaucoma. The laser system can be configured to increase a circumlental space of the eye and increase movement of a posterior vitreous zonule in order to increase accommodation. The light energy may comprise wavelengths strongly absorbed by collagen of the sclera. In many embodiments a heat sink is provided to couple to the conjunctiva and the heat sink comprises a material transmissive to the light energy absorbed by collagen, for example Zinc Selenide. The heat sink can be chilled to inhibit damage to the conjunctiva of the eye. In many embodiments, one or more layers of the epithelium of the eye remain substantially intact above the zone where the eye has been treated when the heat sink has been removed.

17 Claims, 35 Drawing Sheets

Related U.S. Application Data continuation of application No. PCT/US2014/023763, filed on Mar. 11, 2014.

(60) Provisional application No. 61/936,054, filed on Feb. 5, 2014, provisional application No. 61/886,478, filed on Oct. 3, 2013, provisional application No. 61/801,041, filed on Mar. 15, 2013.

(52) U.S. Cl.
CPC ............ *A61F 2009/00868* (2013.01); *A61F 2009/00887* (2013.01); *A61F 2009/00895* (2013.01)

(56) References Cited

U.S. PATENT DOCUMENTS

| | | | |
|---|---|---|---|
| 5,722,952 | A | 3/1998 | Schachar |
| 5,779,696 | A | 7/1998 | Berry |
| 5,997,529 | A | 12/1999 | Tang |
| 6,099,521 | A | 8/2000 | Shadduck |
| 6,334,856 | B1 | 1/2002 | Allen |
| 6,503,231 | B1 | 1/2003 | Prausnitz |
| 6,611,707 | B1 | 8/2003 | Prausnitz |
| 6,679,855 | B2 | 1/2004 | Horn |
| 6,743,211 | B1 | 6/2004 | Prausnitz |
| 6,745,775 | B2 | 6/2004 | Lin |
| 7,189,248 | B2 | 3/2007 | Schachar |
| 7,226,439 | B2 | 6/2007 | Prausnitz |
| 7,344,499 | B1 | 3/2008 | Prausnitz |
| 7,503,916 | B2 | 3/2009 | Shimmick |
| 7,918,814 | B2 | 4/2011 | Prausnitz |
| 8,102,734 | B2 | 1/2012 | Sliwa |
| 8,545,487 | B2 | 10/2013 | Muller |
| 8,663,206 | B2 * | 3/2014 | Schachar ............ A61F 9/0017 606/4 |
| 9,161,857 | B2 | 10/2015 | Mordaunt |
| 10,195,080 | B2 | 2/2019 | Berlin |
| 2001/0016736 | A1 * | 8/2001 | Lin .................... A61F 9/008 606/5 |
| 2002/0049389 | A1 | 4/2002 | Abreu |
| 2002/0082543 | A1 | 6/2002 | Park |
| 2002/0099363 | A1 | 7/2002 | Woodward |
| 2002/0173777 | A1 * | 11/2002 | Sand ................... A61F 9/008 606/4 |
| 2004/0030269 | A1 | 2/2004 | Horn |
| 2004/0030369 | A1 | 2/2004 | Kubota |
| 2004/0093046 | A1 | 5/2004 | Sand |
| 2005/0137531 | A1 | 6/2005 | Prausnitz |
| 2006/0007965 | A1 | 1/2006 | Tankovich |
| 2006/0129141 | A1 | 6/2006 | Lin |
| 2006/0224146 | A1 * | 10/2006 | Lin .................... A61F 9/008 606/4 |
| 2006/0253111 | A1 | 11/2006 | Van Valen |
| 2007/0078471 | A1 | 4/2007 | Schachar |
| 2007/0083190 | A1 | 4/2007 | Domankevitz |
| 2007/0123845 | A1 | 5/2007 | Lubatschowski |
| 2007/0203478 | A1 | 8/2007 | Herekar |
| 2007/0225676 | A1 | 9/2007 | Prausnitz |
| 2008/0015660 | A1 | 1/2008 | Herekar |
| 2008/0039769 | A1 | 2/2008 | Peyman |
| 2009/0149923 | A1 | 6/2009 | Herekar |
| 2009/0157062 | A1 | 6/2009 | Hauger |
| 2009/0182306 | A1 | 7/2009 | Lee |
| 2010/0057060 | A1 | 3/2010 | Herekar |
| 2010/0063174 | A1 | 3/2010 | Ruberti |
| 2010/0114109 | A1 | 5/2010 | Peyman |
| 2010/0152626 | A1 | 6/2010 | Schwartz |
| 2010/0210996 | A1 | 8/2010 | Peyman |
| 2010/0256597 | A1 | 10/2010 | Prausnitz |
| 2010/0312191 | A1 | 12/2010 | Allen |
| 2011/0009779 | A1 | 1/2011 | Romano |
| 2011/0028807 | A1 | 2/2011 | Abreu |
| 2011/0257639 | A1 | 10/2011 | Jones |
| 2011/0282333 | A1 | 11/2011 | Herekar |
| 2012/0029489 | A1 | 2/2012 | Mordaunt |
| 2012/0209051 | A1 | 8/2012 | Blumenkranz |
| 2012/0283804 | A1 | 11/2012 | Kang |
| 2013/0023966 | A1 | 1/2013 | Depfenhart |
| 2013/0158530 | A1 | 6/2013 | Goldshleger |
| 2014/0074013 | A1 | 3/2014 | McCary |
| 2014/0114297 | A1 | 4/2014 | Woodley |
| 2015/0209181 | A1 | 7/2015 | Herekar |
| 2015/0305930 | A1 | 10/2015 | Myung |
| 2015/0320595 | A1 | 11/2015 | Blumenkranz |
| 2016/0000605 | A1 | 1/2016 | Mordaunt |
| 2017/0035975 | A1 | 2/2017 | Myung |

FOREIGN PATENT DOCUMENTS

| | | |
|---|---|---|
| CA | 2330207 | 12/1999 |
| CA | 2510389 | 12/1999 |
| CA | 2376128 | 12/2000 |
| CN | 102917676 A | 2/2013 |
| EP | 1086214 | 3/2001 |
| JP | 2004524871 | 8/2004 |
| JP | 2004526507 | 9/2004 |
| JP | 2009055747 | 3/2009 |
| KR | 1020180108328 | 10/2018 |
| WO | 9012618 | 11/1990 |
| WO | 9012618 A1 | 11/1990 |
| WO | WO0236029 | 5/2002 |
| WO | 02078556 A1 | 10/2002 |
| WO | 2007131050 | 11/2007 |
| WO | 2009094394 | 7/2009 |
| WO | 2011019940 A2 | 2/2011 |
| WO | 2014150601 | 9/2014 |

OTHER PUBLICATIONS

Croft, et al. Accommodation and presbyopia. Int Ophthalmol Clin. 2001 Spring; 41(2):33-46.

Croft, MA et al., "Accommodation and Presbyopia.", International Ophthalmology Clinics., (2001), vol. 41, No. 2, p. 33, XP008090262.

European Search Report and Opinion dated Oct. 4, 2016 for EP2967710.

Hoogenboom, Martijn, et al., "Mechanical High-Intensity Focused Ultrasound Destruction of Soft Tissue: Working Mechanisms and Physiologic Effects," Ultrasound in Medicine and Biology, 41(6):1500-1517 (2015).

International Preliminary Report on Patentability for International Application No. PCT/US2016/055829, 18 pages (dated Apr. 19, 2018).

International Preliminary Report on Patentability for International Application No. PCT/US2017/023092, 13 pages (dated Sep. 27, 2018).

International Search Report and Written Opinion for International Application No. PCT/US2014/023763 (dated Sep. 10, 2014).

International Search Report and Written Opinion for International Application No. PCT/US2016/055829, 21 pages (dated Dec. 27, 2016).

International Search Report and Written Opinion for International Application No. PCT/US2017/023092, 15 pages (dated Jun. 9, 2017).

Mission for Vision. Anatomy of the human eye. http://www.images.missionforvisionusa.org/anatomy/2005/10/ciliary-body-histology-answers.html. Oct. 24, 2005. Accessed on Feb. 10, 2016. 4 pages.

Poley, et al. Intraocular pressure reduction after phacoemulsification with intraocular lens implantation in glaucomatous and nonglaucomatous eyes: evaluation of a causal relationship between the natural lens and open-angle glaucoma. J Cataract Refract Surg. Nov. 2009; 35(11):1946-55. doi: 10.1016/j.jcrs.2009.05.061.

Poley, et al. Long-term effects of phacoemulsification with intraocular lens implantation in normotensive and ocular hypertensive eyes. J Cataract Refract Surg. May 2008; 34(5):735-42. doi: 10.1016/j.jcrs.2007.12.045.

Rosales, et al. Changes in crystalline lens radii of curvature and lens tilt and decentration during dynamic accommodation in rhesus monkeys. J Vis. Jan. 28, 2008; 8(1):18.1-12. doi: 10.1167/8.1.18.

(56) References Cited

OTHER PUBLICATIONS

Rosales, P et al., "Changes In Crystalline Lens Radii of Curvature and Lens Tilt and Decentration During Dynamic Accommodation In Rhesus Monkeys.", Journal of Vision., (Jan. 28, 2008), vol. 8, No. 1, p. 1, XP055287692.

Strenk, et al. Age-related changes in human ciliary muscle and lens: a magnetic resonance imaging study. Invest Ophthalmol Vis Sci. May 1999; 40(6):1162-9.

Strenk, et al. High resolution MRI study of circumlental space in the aging eye. J Refract Surg. Sep.-Oct. 2000; 16(5):S659-60.

Strenk, et al. Magnetic resonance imaging of aging, accommodating, phakic, and pseudophakic ciliary muscle diameters. J Cataract Refract Surg. Nov. 2006; 32(11):1792-8.

Strenk, et al. Magnetic resonance imaging of the anteroposterior position and thickness of the aging, accommodating, phakic, and pseudophakic ciliary muscle. J Cataract Refract Surg. Feb. 2010; 36(2):235-41. doi: 10.1016/j.jcrs.2009.08.029.

Strenk, et al. The mechanism of presbyopia. Prog Retin Eye Res. May 2005; 24(3):379-93. Epub Dec. 19, 2004.

Gevorkian et al., "Thermal (In) Stability of Type I Collagen Fibrils", Physical Review Letters 102, pp. 048101-048104 (2009).

Muller et al., "Imaging thermal expansion and retinal tissue changes during photocoagulation by high speed OCT", Biomed. Optics Express vol. 3, No. 5, pp. 1025-1046 (2012).

Vangsness et al., "Collagen shortening. An experimental approach with heat", Clinical Orthopedics and Related Research, No. 337, pp. 267-271 (1997).

\* cited by examiner

FIG. 28

SCLERAL TRANSLOCATION ELASTO-MODULATION METHODS AND APPARATUS

CROSS-REFERENCE

The present application is a continuation of U.S. patent application Ser. No. 14/854,390, filed Sep. 15, 2015, which is a continuation of International Application No. PCT/US14/023763, filed Mar. 11, 2014, published as WO 2014/150601 on Sep. 25, 2014, which claims priority to U.S. Provisional Application No. 61/801,041, filed Mar. 15, 2013, and to U.S. Provisional Application No. 61/886,478, filed Oct. 3, 2013, and to U.S. Provisional Application No. 61/936,054, filed Feb. 5, 2014, the entire disclosures of which are incorporated herein by reference.

BACKGROUND

The field of the present invention is related generally to medical devices and methods, and more particularly relates to methods and apparatus for treating the eye.

Existing methods and apparatus for treating presbyopia and glaucoma can produce less than ideal results. For example, multifocal lenses can degrade vision with at least some blur at near vision and far vision. Prior attempts at restoring natural movement of the lens have resulted in less than ideal results in at least some instances. Although accommodating intraocular lenses (hereinafter "IOLs") have been used, these accommodating lenses can provide less than ideal amounts of accommodation in at least some instances. Also, prior methods and apparatus for treating glaucoma can be less than ideal in at least some instances.

In light of the above, it would be beneficial to provide improved methods and apparatus for treating presbyopia and glaucoma. Ideally, such methods and apparatus would restore accommodation in the natural lens of the eye and provide improved accommodation with accommodating IOLs.

SUMMARY

Embodiments of the present invention provide improved methods and apparatus for treatment of the eye. The methods and apparatus as disclosed herein provide improved treatments of one or more of presbyopia or glaucoma, and in many embodiments both. Although many embodiments are described with reference to a natural lens of the eye, the embodiments disclosed herein can be used to improve accommodation with accommodating IOLs.

In many embodiments, the eye is treated such that the posterior vitreous zonules can move at least anteriorly to allow the lens capsule to move anteriorly or reshape, or both, in order to provide improved accommodation. In many embodiments, the eye is treated in order to provide improved anterior-centripetal movement of the ciliary body at the insertion of the posterior vitreous zonule into the ciliary body. Alternatively or in combination, the eye can be treated so as to increase the circumlental space between the ciliary body and lens capsule in order to provide increased amounts of accommodation. The increased amount of anterior movement of the posterior vitreous zonule from the unaccommodated state to the accommodative state can be within a range from about 250 to about 1000 um, for example.

The sclera can be softened posterior to the lens equator and anterior to the insertion location of the posterior zonules near the ora serrata in one or more of many ways in order to encourage movement of the posterior vitreous zonules at least anteriorly in order to provide improved accommodation, such as with one or more of light energy, ultrasound energy, electrical energy, heating, electroporation, optoporation, or photonic desincrustation or galvanic desincrustation. In many embodiments, the softening of the scleral tissue posterior to the lens equator provides at least about one millimeter of anterior movement of the posterior vitreous zonules lens and/or capsule so as to provide at least about one diopter of accommodation. In many embodiments, the movement of the posterior vitreous zonules near the insertion into the ora serrata allows the lens to move anteriorly and to reshape itself with a more convex curvature. In many embodiments, the sclera is softened without removal of collagen from the tissue, which can inhibit regression of the softening effect. The softening of the sclera can be performed so as to inhibit damage to the ciliary body and choroid, and the energy such as light energy can be directed in a manner that avoids the ciliary body and choroid. The scleral softening can be performed such that the zonules of the eye comprise slack subsequent to treatment in order to inhibit changes in the position of the lens and/or capsule when the eye is configured for far vision and inhibit changes to the far vision refraction of the eye. In many embodiments, the posterior vitreous zonules comprise at least some slack in order to allow the lens capsule to move anteriorly. In many embodiments, the softened scleral tissue between the lens equator and insertion of the posterior vitreous zonules at the ora serrata moves interiorly toward an optical axis of the eye when the eye accommodates, and may provide inward movement of the posterior vitreous zonules. In many embodiments, the scleral tissue is translocated near the ciliary body apex in order to increase the circumlental space. The translocation of the scleral tissue and ciliary body apex can be performed without tissue removal, in order to decrease regression of an initial effect and in order to decrease the invasiveness of the procedure.

In many embodiments, light energy is used to soften the tissue, and the light energy comprises wavelengths that are strongly absorbed by the collagen of the sclera or the water of the sclera, or both for example. In many embodiments, the light energy comprises wavelengths that are absorbed more strongly by stromal tissue than water, for example light comprising a wavelength within a range from about 4 to 6 um, such as from about 5.5 to 6.6 um. The light energy absorbed more strongly by stroma than water has the advantage of providing more accurate treatment with less interference with water, and can allow the tissues of the eye to retain healthy amounts of water during treatment, for example tissues of the conjunctiva of the eye. Also, interference from water based surgical fluids such as saline and anesthetics can be substantially inhibited.

In many embodiments a heat sink is provided to couple to the conjunctiva and the heat sink comprises a material transmissive to the light energy, such as sapphire or Zinc Selenide (hereinafter "ZnSe"). The heat sink material can be configured to transmit light energy absorbed more strongly by the stroma than water, and may comprise Zinc Selenide (hereinafter "ZnSe"), for example. The heat sink can be chilled to inhibit damage to the conjunctiva of the eye. The heat sink can provide improved transmission of light energy when condensation is present, as the condensed water may be less strongly absorbed by the laser beam. In many embodiments, one or more layers of the epithelium of the eye (basal layer, wing layer or squamous layer) remains substantially intact above the zone where the eye has been treated, for example at least one layer of viable epithelial cells can remain intact when the heat sink is removed.

In many embodiments, the optically transmissive material of the heat sink is shaped and optically configured with smooth surfaces so as to comprises an optically transparent heat sink such as a lens. The heat sink may comprise a window of the optically transmissive material, and can be one or more of many shapes such as a flat on opposing surfaces, plano-concave, or convex-concave. The convex-concave heat sink window may comprise a meniscus shaped lens, having substantial optical power or no substantial optical power, for example.

The location of the heat sink can be fixed in relation to a fixed structure of the laser system in order to fix the location of the eye, and the heat sink may comprise one or more curved surfaces such as a concave surface to engage the eye. In many embodiments, an arm extends from the fixed structure of the laser system to the heat sink in order to fix the location of the heat sink.

The laser may comprise one or more of many lasers emitting one or more of many wavelengths, such as infrared lasers. In many embodiments, the laser comprises a quantum cascade laser configured to emit light having a wavelength within a range from about 5.8 to about 6.6 um, for example from about 6 to about 6.25 um. Such lasers are commercially available, and con be configured by a person of or In many embodiments the treatment apparatus comprises an energy source such as a laser and a docking station to retain the eye. In many embodiments the docking station comprises a chilled optically transmissive heat sink to couple to the eye. The docking station couples to the eye such that the heat sink contacts the conjunctiva of the eye and fixes the working distance of the eye from the surgical laser, such that the scleral treatment comprising softening posterior to the lens equator can be performed accurately. In many embodiments, heat sink is chilled such that at least one epithelial layer of the conjunctiva of the eye above the treated tissue remains viable, in order to expedite healing of the eye and decrease invasiveness of the procedure. The chilled heat sink structure can be chilled to a temperature within a range from above the freezing temperature of the eye and saline, at about −3 degrees Celsius (C), to below an ambient room temperature of about 20 degrees Celsius. Alternatively, a heat sink can be provided without chilling. In many embodiments, the freezing temperature of the eye corresponds to the freezing temperature of saline, about −3 degrees, for example. In many embodiments, the apparatus comprises a scanner to scan the laser beam. The laser beam can be pulsed or continuous, and in many embodiments comprises a continuous laser beam configured to inhibit temperature spikes related to ablation of the eye. In many embodiments the laser irradiance comprises a temporal and spatial profile to inhibit transient heating peaks of the tissue that can be related to removal of tissue such as ablation. The scanner can be configured to scan the laser beam in a plurality of quadrants, such as for quadrants with untreated regions between each of the quadrants to inhibit damage to muscles of the eye located between the treatment quadrants.

While reference is made to softening tissue with light energy, other forms of energy can be used to soften tissue such as one or more of electroporation, microwave, thermal, electrical energy or di-electrophoretic energy and combinations thereof. In many embodiments, electroporation needles can be provided with a shaped array having four quadrants sized to extend through the conjunctiva and deliver electroporation energy beneath the conjunctiva. Alternatively, shaped contact electrodes can be provided without needles such that the current is passed through the epithelial layer of the conjunctiva to targeted regions of the sclera in order to soften at least a portion of the scleral tissue between the lens equator and insertion location of the posterior vitreous zonules. The electroporation to soften the sclera comprises an oscillating electric field to pass current in an electroporation treatment profile similar to the optical treatment profile disclosed herein.

The embodiments disclosed herein provide improved accommodation of the eye with an increase of one or more of the perilenticular space or a softened and/or plasticized portion of scleral or corneal tissue. The perilenticular space extending between the ciliary body and the lens of the eye can be increased with tissue stabilization and shrinking. In some embodiments, the perilenticular space is increased with cross-linking of an outer portion of a sclera of the eye near a ciliary body of the eye so as to stabilize the outer portion of scleral tissue with increased stiffness, and an inner shrinking treatment of an inner portion of the sclera located inwardly from the outer portion and toward the lens of the eye. The shrinking of the inner portion can be combined with the stabilization of the outer portion such that the inner surface of the ciliary body is urged away from the lens capsule so as to increase the perilenticular space. The portion of softened and/or plasticized scleral tissue can be located between sclera disposed over the ora serrata and sclera corresponding to the equator of the lens of the eye in order to allow the lens capsule and lens to move an increased amount in order to restore accommodation. The softening and/or plasticizing of the scleral tissue portion can provide improved accommodation with increased mobility of the posterior vitreous zonules extending between the ciliary body and the ora serrata. In many embodiments, the stiffening of the outer portion of the sclera and shrinking of the inner portion of the sclera provides improved drainage of the channels of the trabecular meshwork of the eye, and can be related to increased channel sizes of this tissue structure.

In many embodiments, tissue stabilization and shrinking can be used to treat glaucoma. An outer portion of the sclera can be treated with cross-linking to add stiffness and stabilize the outer portion. An inner portion disposed inwardly from the outer portion can be treated with shrinking in order to urge one or more tissue structures of the eye toward the stabilized portion and increase channel sizes of the one or more tissue structures of the eye such as Schlemm's canal and one or more channels of the trabecular meshwork.

In an aspect, a method is provided for treating an eye. The method can include cross-linking an outer portion of the eye and shrinking an inner portion of the eye, such that a tissue structure of the eye has moved outwardly toward the cross-linked outer portion when the inner portion has shrunk. Outward can include radially outward away from an optical axis of the eye.

In many embodiments, the outer portion can include a sclera of the eye through which a plane defining an equator of the lens of the eye extends in order to treat a presbyopia of the eye. The outer sclera portion can include a cross-linked profile prior to shrinking. The cross-linked profile can be substantially maintained when the inner portion shrinks. A cross-sectional thickness of the sclera can extend from an outer surface of the sclera adjacent a conjunctiva to an inner surface of the sclera adjacent a trabecular meshwork through the outer portion and the inner portion. The cross-sectional thickness of the sclera can decrease from a first thickness prior to shrinking to a second thickness subsequent to shrinking, the second thickness less than the first thickness. The inner surface can include an inner surface profile extending along an inner side of the sclera. The outer surface can include an outer surface profile extending along an outer side of the sclera. The inner surface can deflect outwardly an amount greater than the outer surface deflects inwardly when the inner portion has shrunk.

In many embodiments, the tissue structure of the eye can include a ciliary body of the eye in order to increase a perilenticular space of the eye. The tissue structure of the eye can include one or more of a portion of the cornea or a portion of the sclera lateral to the Schlemm's canal in order to increase a cross-sectional size of one or more of the Schlemm's canal or a trabecular meshwork of the eye in order to treat glaucoma of the eye. The tissue structure of the eye can include a portion of the sclera lateral to a trabecular meshwork of the eye in order to increase a cross-sectional size of channels of the trabecular meshwork in order to treat glaucoma of the eye.

In many embodiments, the eye includes a conjunctiva disposed over a sclera and the inner portion is treated through the conjunctiva of the eye. The eye can include a conjunctiva and the conjunctiva can be moved away from the sclera to treat the inner portion.

In many embodiments, the outer portion can be cross-linked with a cross-linking agent including one or more of: riboflavin, rose bengal, methylene blue, indocyanine green, genipin, threose, methylglyoxal, glyceraldehydes, aliphatic β-nitro alcohols, or black currant extract, or an analog of any of the above. The inner portion can shrink with one or more of thermal energy, radiofrequency energy, electrical energy, microwave energy, or light energy. The method can include placing a heat sink over the outer portion to conduct heat away from the outer portion when the inner portion is heated. The inner portion can shrink with light energy and the heat sink can include a material transmissive to wavelengths of the light energy in order to heat the tissue with light energy absorbed beneath the heat sink. The inner portion can be heated to a temperature within a range from about 50 to about 70 degrees Centigrade in order to shrink the tissue. The portion can be heated within the range without substantially weakening the tissue. A layer of conjunctiva located above the inner portion can remain substantially viable when the inner portion is treated in order to inhibit pain and swelling.

In many embodiments, the method can include softening a portion of scleral tissue of the eye, the sclera tissue extending posterior to an equatorial plane of a lens of the eye and anterior to an insertion location of posterior vitreous zonules proximate an ora serrata of the eye. The portion can be heated to a temperature within a range from about 70 to about 90 degrees Centigrade in order to weaken the tissue. The softened portion can include four softened portions, each corresponding to four locations away from muscles of the eye including inferior muscles, superior muscles, nasal muscles, and temporal muscles in order to inhibit damage to the muscles.

In another aspect, a method for treating an eye is provided. The method can include softening a portion of sclera tissue of the eye, the portion of sclera tissue extending posterior to an equatorial plane of a lens of the eye and anterior to an insertion location of posterior vitreous zonules proximate an ora serrata of the eye.

In another aspect, an apparatus to perform the method of any of the preceding embodiments is provided.

In another aspect, an apparatus to treat the eye is provided. The apparatus can include a cross-linking agent to cross-link an outer portion of a sclera of the eye. The apparatus can include an energy source to shrink an inner portion of the sclera of the eye and move a tissue structure outward toward the outer portion when the inner portion has shrunk. The cross-linking agent can include one or more of a chemical agent or photosensitizers. The energy source can include one or more of a light energy source, a thermal energy source, an electrical energy source, an RF energy source, or a microwave energy source. The energy source can include a microelectrode array. The cross-linker can include a chemical photosensitizer.

In many embodiments, the energy source can include a light energy source, in which the light energy source configured to emit at least one wavelength of light to cross-link the outer portion and shrink the inner portion. The light source can include a single light source to emit a wavelength of light to cross-link the outer portion and shrink the inner portion, optionally, to shrink the inner portion and cross-link the outer portion together, or optionally, to shrink the inner portion after the outer portion has been cross-linked, and combinations thereof. The light source can include a first light source to cross-link the outer portion and a second light source to shrink the inner portion. The first light source can be configured to emit a first light energy including a first wavelength of light and the second light source can be configured to emit a second light energy including a second wavelength of light, the first wavelength different from the second wavelength. The light source can include a softening light source to soften a tissue of the sclera.

In another aspect, a method of treating an eye is provided. An inner portion of the eye is shrunk to cause a tissue structure of the eye to move outwardly toward an outer portion of the eye.

In another aspect, an apparatus configured to perform the method of any one of the preceding embodiments is provided.

These and other embodiments are described in further detail in the following description related to the appended drawings.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

A better understanding of the features and advantages of the present disclosure will be obtained by reference to the following detailed description that sets forth illustrative embodiments, in which the principles of the disclosure are utilized, and the accompanying drawings of which:

FIG. 28 shows a user interface, in accordance with embodiments; and

DETAILED DESCRIPTION

Figure 1:
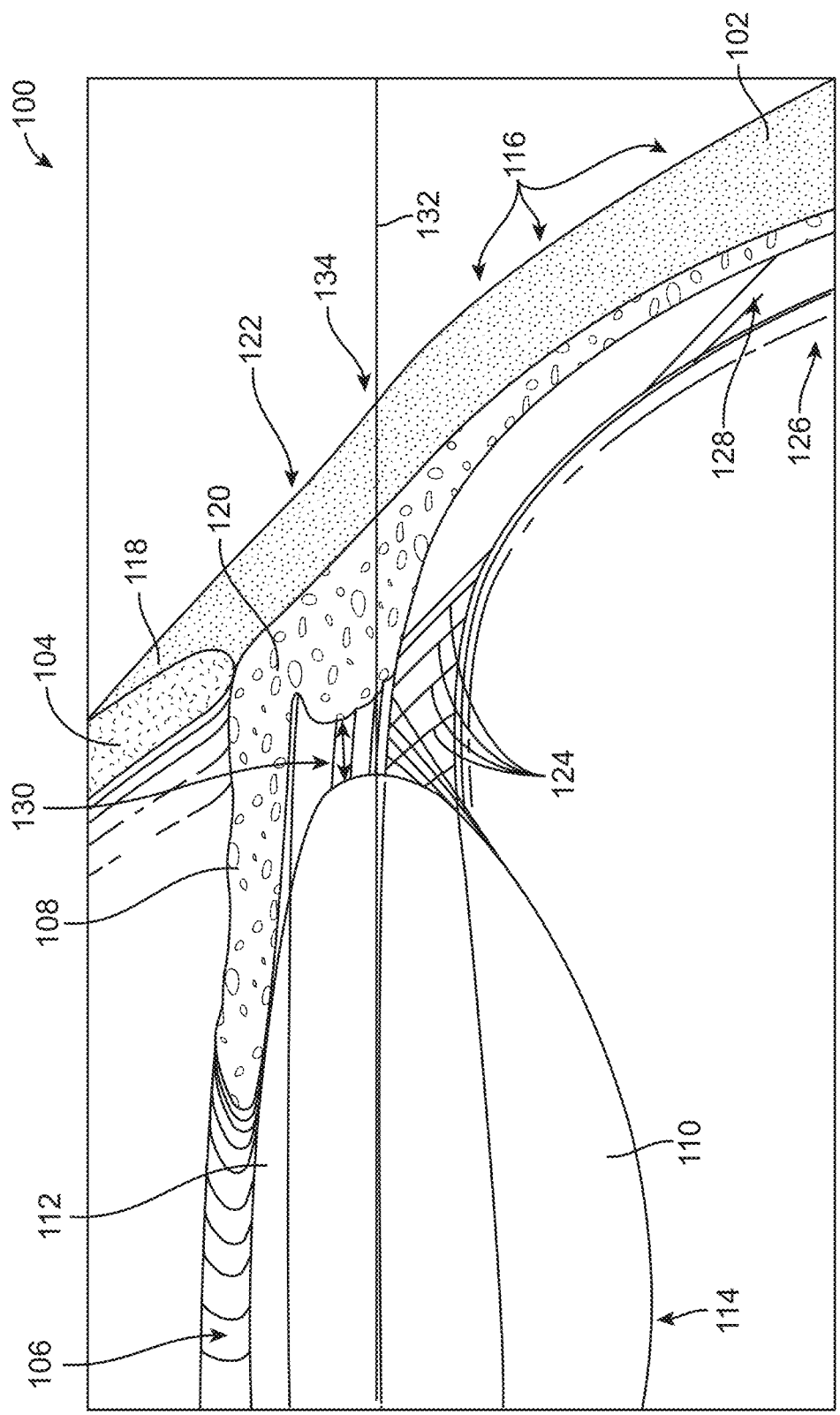
FIG. 1 illustrates a presbyopic eye in a configuration for far vision, in accordance with embodiments.

A better understanding of the features and advantages of the present disclosure will be obtained by reference to the following detailed description that sets forth illustrative embodiments, in which the principles of embodiments of the present disclosure are utilized, and the accompanying drawings.

Although the detailed description contains many specifics, these should not be construed as limiting the scope of the disclosure but merely as illustrating different examples and aspects of the present disclosure. It should be appreciated that the scope of the disclosure includes other embodiments not discussed in detail above. Various other modifications, changes and variations which will be apparent to those skilled in the art may be made in the arrangement, operation and details of the method and apparatus of the present disclosure provided herein without departing from the spirit and scope of the invention as described herein.

The embodiments disclosed herein can be combined in one or more of many ways to provide improved methods and apparatus for treating the eye.

As used herein like characters identify like elements.

As used herein A and/or B encompasses one or more of A or B, and combinations thereof such as A and B.

The embodiments as disclosed herein provide improved methods and apparatus for the treatment of one or more of presbyopia or glaucoma, in accordance with embodiments. For example, presbyopia treatments as disclosed herein can have a beneficial effect on a patient's intraocular pressure (hereinafter "IOP"). Alternatively or in combination, the treatment can be directed to the treatment of glaucoma, for example. The treatments and apparatus disclosed herein can be combined with many known methods and apparatus for treatment. For example, the restoration of accommodation as described herein can be combined with one or more of many known prior accommodating IOLs, for example. Alternatively or in combination, the methods and apparatus as disclosed herein can be combined with one or more known glaucoma therapies.

Provisional Application to U.S. App. Ser. No. 61/801,041, filed on Mar. 15, 2013, which has been previously incorporated herein by reference, discloses improved methods and apparatus to treat presbyopia and/or glaucoma in accordance with many embodiments disclosed herein. In many embodiments, tissue is not substantially removed and is moved to a new location with the treatment. This movement of collagenous tissue from a first location to a second location provides improved treatment with less regression of effect and healing. The methods and apparatus disclosed therein describe treatment of the eye without ablation and without formation of hard spots as can be formed when a laser removes tissue with heat. In many embodiments, the treatment can be performed without incisions of the eye, in order to decrease the invasiveness of the procedure and decrease regression of effect.

In many embodiments, the methods and apparatus disclosed herein provide scleral translocation and elasto-modulation (hereinafter "STEM") of an eye in order to at least partially restore accommodation of the eye and treat presbyopia or glaucoma.

In many embodiments, the STEM procedure provides extra-corneal and/or extra-lenticular laser treatment to soften and/or plasticize the sclera and/or peripheral cornea. The STEM procedure can provide non-reductive and non-ablative restoration of accommodative power compatible with the Helmholtz theory of accommodation. Treatment can be applied to the eye from the scleral spur to the ora serrata while avoiding damage to limbal stem cells, conjunctiva, epithelium, and eye muscles. The STEM procedure can include elasto-modulation to one or more of: soften and/or plasticize scleral regions near the ciliary body apex to enhance inward movement of the ciliary body during accommodation; soften and/or plasticize scleral regions near the insertions of the posterior vitreous zonules to enhance anterior movement of the ciliary body during accommodation; or soften and/or plasticize regions of the sclera and/or cornea near the sclera spur to enhance corneal asphericity and/or flexing during accommodation.

In many embodiments, the STEM procedure provides application of heat to the eye to produce a thermo-mechanical response in a tissue of the eye, such as in the cornea and/or sclera. For example, the cornea and/or sclera can be heated to between 60° C. and 70° C. to produce shrinkage of the tissue. Heating of the cornea and/or sclera to a temperature within this range can also produce softening and/or plasticizing (e.g., to approximately 10% of the native strength of the tissue). The cornea and/or sclera can be heated to greater than 80° C. of the eye to produce denaturation of the tissue.

The STEM procedure may provide one or more of the following advantages:

Increased depth of field of the eye;

Preservation of distance visual acuity, as the central corneal and central lenticular regions are substantially unaffected by the treatment;

Preservation of limbal stem cells, ciliary muscle function, conjunctiva, epithelium, and aqueous production, as these are substantially unaffected by treatment;

No substantial loss of contrast sensitivity;

No substantial disturbances of night vision;

Preservation of aesthetics of the eye, as there are no cuts, implants, or full punctures of the eye;

Rapid patient recovery, as the conjunctiva is protected during treatment;

Tolerable treatment procedure for many patients;

Improved safety of the treatment procedure;

Little additional optical power required, resulting in substantially no cross blurring; or Other surgeries, including additional STEM treatments, are not precluded.

FIG. 1 illustrates a presbyopic eye 100 in a configuration for far vision, in accordance with embodiments. The eye 100 includes a sclera 102, a cornea 104, a pupil 106, an iris 108, and a lens 110 within a lens capsule, the lens capsule including a lens capsule anterior surface 112 and a lens capsule posterior surface 114. The sclera is lined by a conjunctiva 116 and includes a sclera spur 118 adjacent the cornea 104. A ciliary body 120 is adjacent the ciliary body sclera region 122. The ciliary body 120 is connected to the lens 110 by vitreal zonules 124 and to the ora serrata 126 by the posterior vitreal zonules 128 (hereinafter "PVZ"). A circumlental space 130 (hereinafter "CLS") is defined by the distance between the lens 110 and the ciliary body 120 along a lens equator plane 132, the lens equator plane 132 passing through an equatorial sclera region 134.

Figure 2:
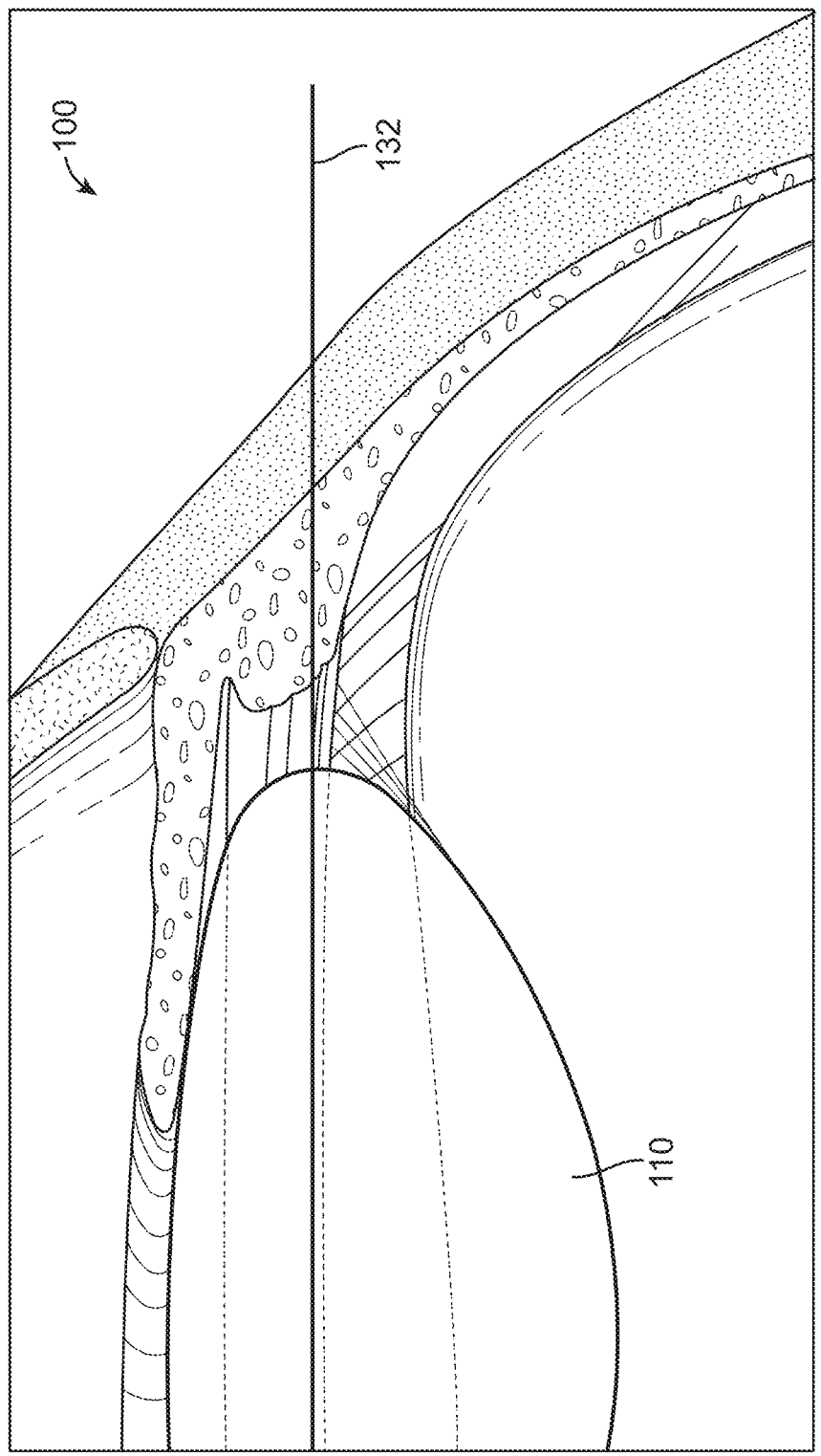
FIG. 2 illustrates the presbyopic eye of FIG. 1 attempting to correct for near vision, in accordance with embodiments.

FIG. 2 illustrates the presbyopic eye 100 of FIG. 1 attempting to correct for near vision, in accordance with embodiments. In the presbyopic eye 100, the curvature of the lens 110 does not change substantially from the curvature in the far vision configuration, and the accommodative amplitude of the lens 110 along the lens equator plane 132 is relatively small.

Table 1 shows PVZ mobility and CLS size in non-presbyopic and presbyopic eyes during an un-accommodative state ("UN-ACC") and an accommodative state ("ACC"). In non-presbyopic eyes, the length of the PVZ changes from 4.6 mm in the un-accommodative state to 3.6 mm in the accommodative state, for a net change of 1 mm. In contrast, PVZ mobility is substantially reduced in presbyopic eyes: the PVZ length changes from 4.6 mm in the un-accommodative state to 4.45 mm in the accommodative state, for a net change of only 0.15 mm. Additionally, the size of the CLS is significantly smaller in presbyopic eyes compared to non-presbyopic eyes, with measured values of 0.68 mm and 0.35 mm in the un-accommodative state, and 0.68 mm and 0.2 mm in the accommodative state, respectively.

TABLE 1

PVZ mobility and CLS size in non-presbyopic and presbyopic eyes.

| | Non-Presbyopic | | | Presbyopic | | |
|---|---|---|---|---|---|---|
| | UN-ACC | ACC | Change | UN-ACC | ACC | Change |
| PVZ (mm) | 4.6 | 3.6 | 1 | 4.6 | 4.45 | 0.15 |
| CLS (mm) | 0.68 | 0.68 | 0 | 0.35 | 0.2 | 0.15 |

Without being bound to any particular theory, it is believed that accommodative anterior and inward ciliary apex movement is hindered by PVZ immobility in the presbyopic eye. The embodiments disclosed herein can provide improved mobility of the accommodative anterior and inward ciliary apex movement with softening of the scleral and corneal tissue as disclosed herein. The embodiments disclosed herein can provide compensation for antero-posterior lens growth, equatorial-apex position and zonular insertion angle changes, and loss in corneal elasticity with age. The embodiments disclosed herein can provide increased curvature of the lens with decreased zonular tension in order to provide increased accommodation. In many embodiments, the simultaneous expansion of the perilenticular space and softened and/or plasticized mid-scleral stroma near the ciliary body and PVZ as described herein can provide for stable distance vision (e.g., augmented by cross-linking) and restoration (e.g., an increase) of accommodative amplitude.

Figure 3:
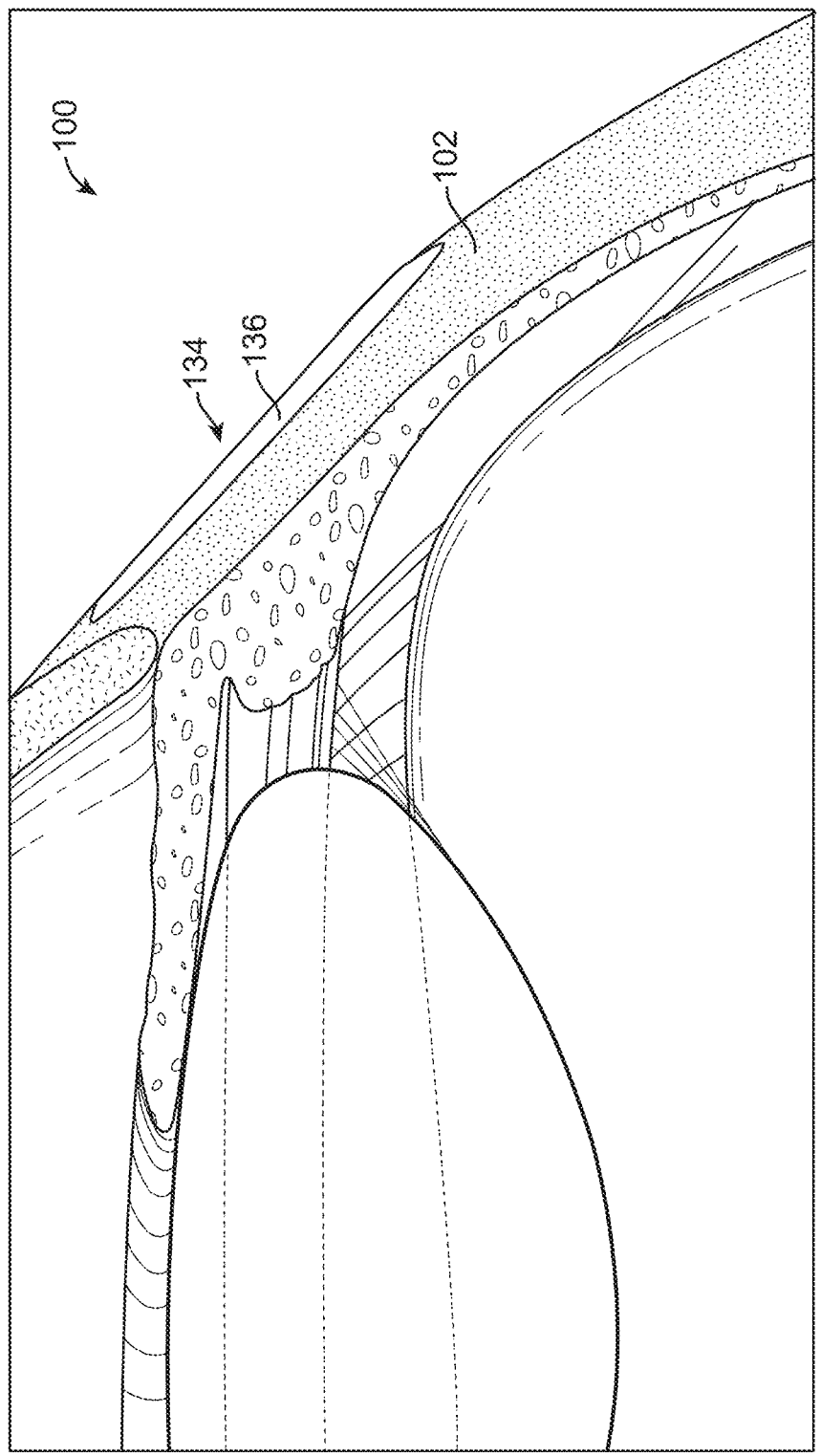
FIG. 3 illustrates stabilization of an eye by cross-linking to treat presbyopia, in accordance with embodiments.

FIG. 3 illustrates stabilization of an eye 100 by cross-linking to treat presbyopia, in accordance with embodiments. The stabilized region 136 can be disposed in the outer portion of equatorial sclera region 134 of the sclera 102. Any suitable stabilization method, such as collagen cross-linking, can be used to stabilize the cross-linked region 136 in order to substantially maintain the outer profile of the sclera 102. In many embodiments, a cross-linking agent is applied to the sclera and allowed to infuse into the sclera at stabilized region 136. An energy source can be applied to the sclera to cross-link the sclera at stabilized region 136 with the cross-linking agent. The energy source can include a microelectrode array to generate a patterned cross-linked profile on the sclera. The energy can include one or more of thermal energy, radiofrequency (hereinafter "RF") energy, electrical energy, microwave energy, or light energy.

In many embodiments, the cross-linking agent includes one or more of many known chemical photosensitizers in the presence of oxygen. Oxygen can be delivered to the stabilized region 136 of the sclera, concurrently with the cross-linking agent or separately. The cross-linking agent can be exposed to light energy when the cross-linking agent has been provided to the tissue, in order to provide cross-linking to a target depth of tissue stabilization. The light energy may include one or more of visible light energy, ultraviolet (hereinafter "UV") light energy, or infrared (hereinafter "IR") light energy. Alternatively or combination, the cross-linking agent may include a chemical cross-linking agent. In many embodiments, the cross-linking agent includes one or more of the following: riboflavin, rose bengal, methylene blue, indocyanine green, genipin, threose, methylglyoxal, glyceraldehydes, aliphatic β-nitro alcohols, black currant extract, or an analog of any of the above.

Figure 4:
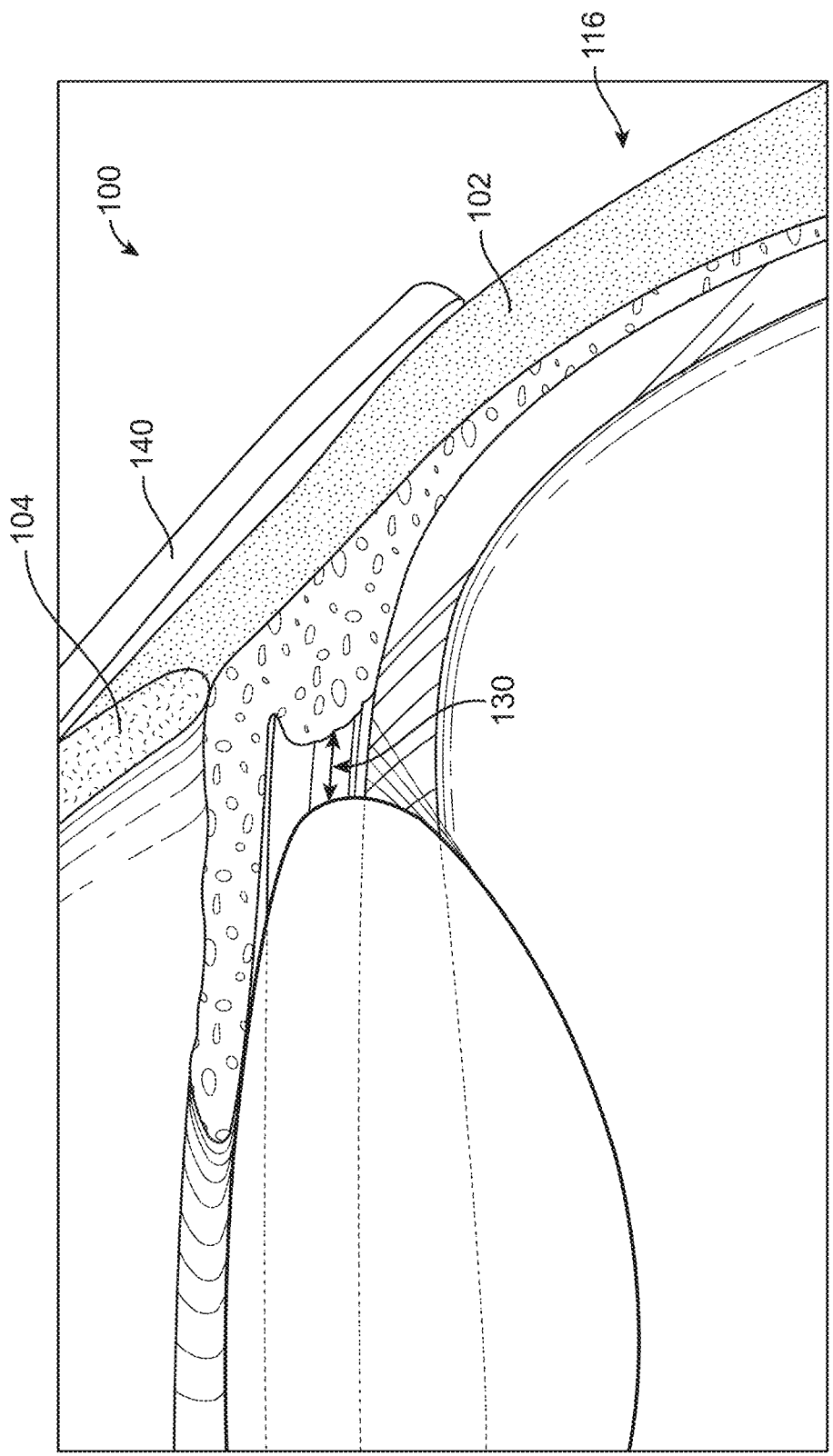
FIG. 4 illustrates a heat sink placed over the eye of FIG. 3 to treat presbyopia, in accordance with embodiments.
Figure 5:
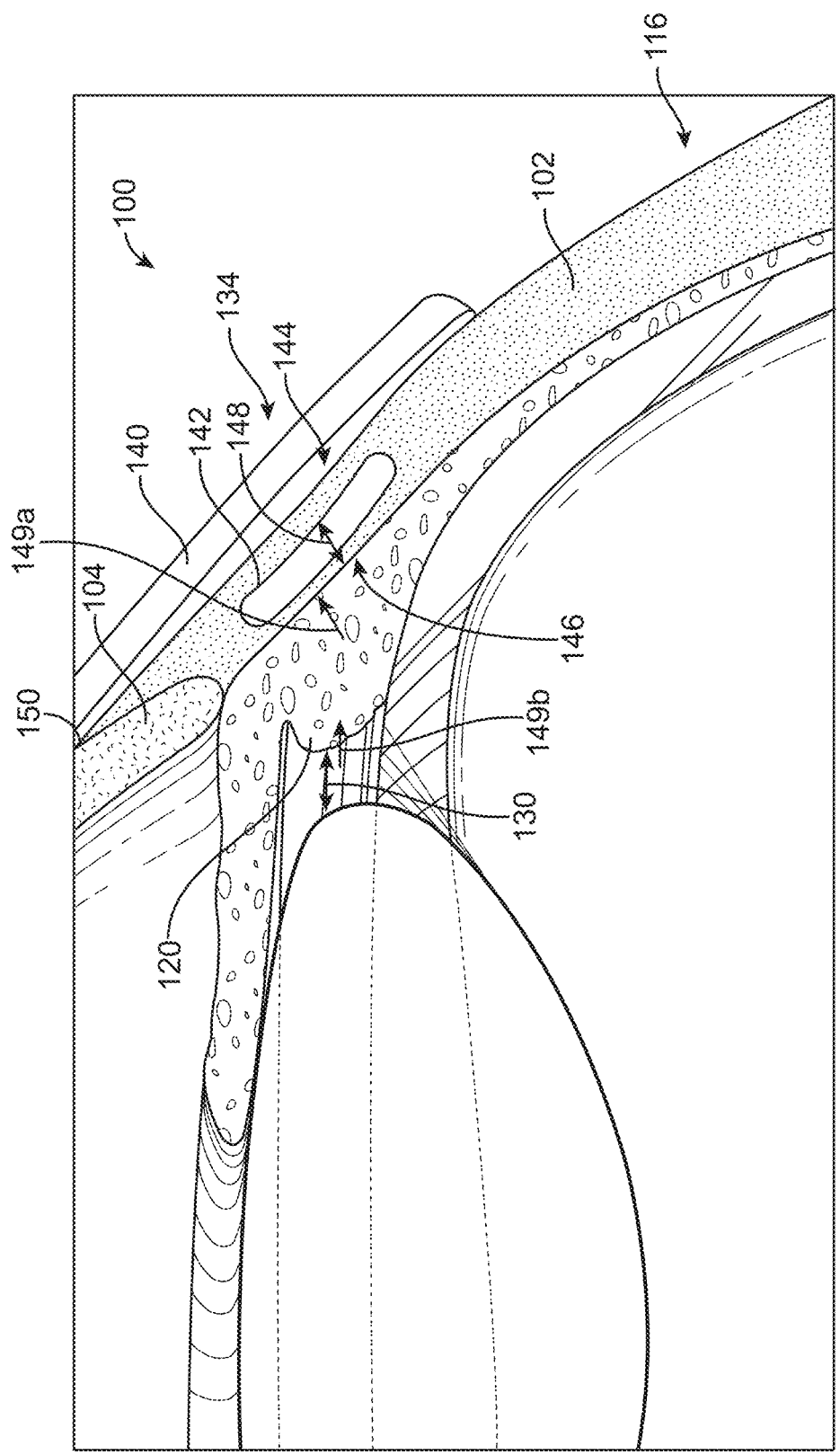
FIG. 5 illustrates a planned treatment zone to expand the circumlental space in the eye of FIG. 4 to treat presbyopia, in accordance with embodiments.
Figure 6:
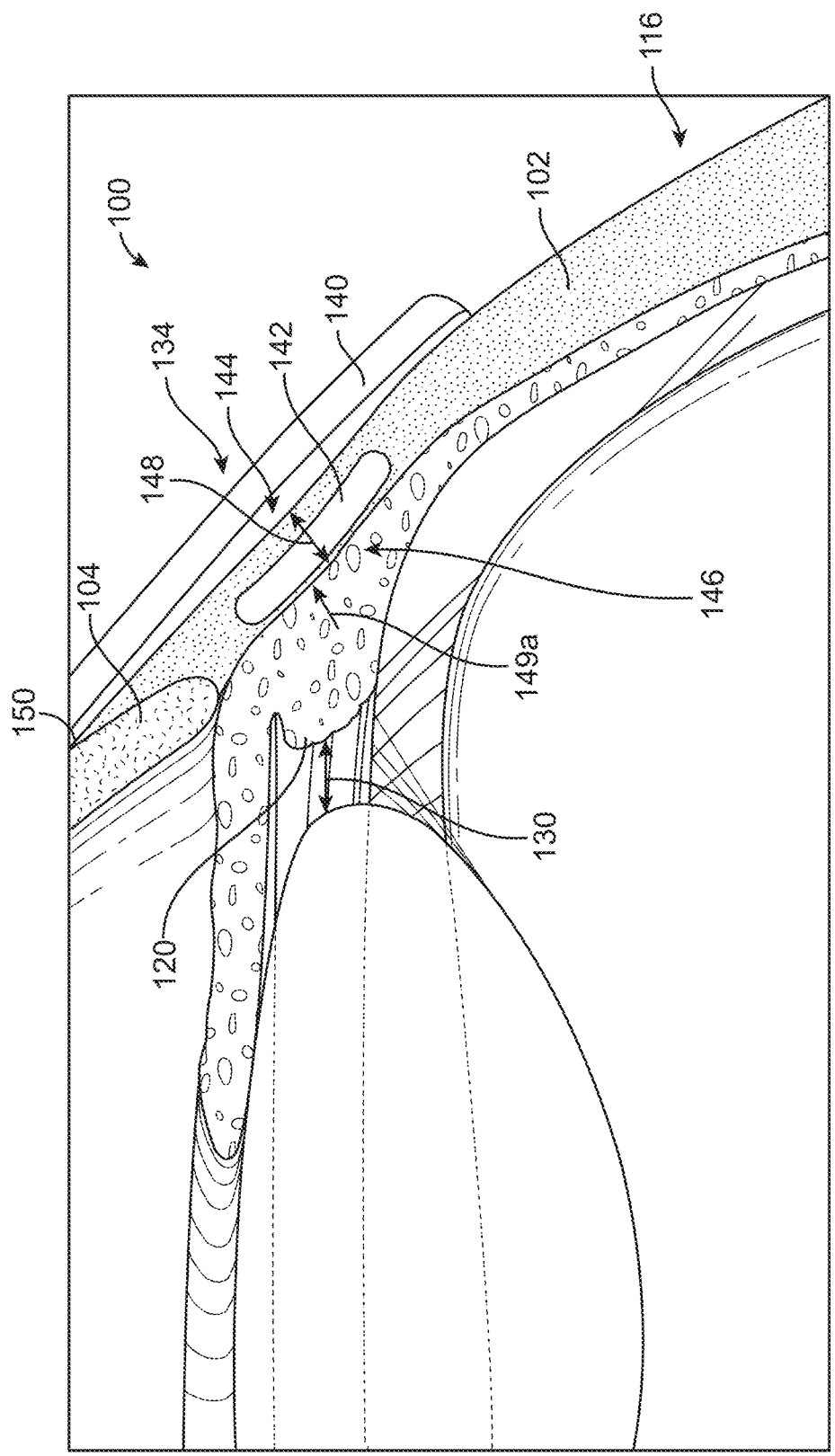
FIG. 6 illustrates laser treatment of the eye of FIG. 5 to treat presbyopia, in accordance with embodiments.

FIGS. 4-6 illustrate aspects of a STEM treatment procedure to expand the CLS and thereby enhance ciliary body apex mobility in order to increase the accommodative amplitude of the eye, in accordance with embodiments. The CLS can be expanded by applying energy to shrink and/or plasticize an inner portion of the eye, such as the inner portion of the sclera (e.g., the mid-stroma), so as to move the ciliary body apex outward and thereby increase the ciliary ring diameter. In many embodiments, the outward movement includes a radially outward movement away from the optical axis of the eye and towards a stabilized outer portion of the eye (e.g., the cross-linked region 136). The energy to shrink and/or plasticize the inner portion of the eye can include one or more of thermal energy, RF energy, electrical energy, microwave energy, or light energy. The energy can shrink and/or plasticize the tissue by heating the tissue to a suitable temperature without substantially weakening the tissue, such as within a range from about 50° C. to 70° C. Heating the tissue can increase the elasticity of the tissue. In many embodiments, the heat is applied such that the outer portion of the tissue remains substantially viable so as to inhibit post-operative pain and swelling. While in many embodiments the energy can be applied through the conjunctiva and/or epithelium, the energy can also be applied with the conjunctiva and/or epithelium moved away from the sclera. The energy source can be the same energy source used to cross-link the eye, as described herein, or a different energy source.

FIG. 4 illustrates a heat sink 140 placed over the eye 100 of FIG. 3 in order to treat presbyopia, in accordance with embodiments. The heat sink 140 can be inserted over an outer portion of the eye 100 including the cornea 104, sclera 102, and conjunctiva 116, in order to conduct heat away from the outer portion of the eye 100 during the treatment procedure. The heat sink can be made of any suitable material. For example, the heat sink can include a material transmissive to wavelengths of light energy (e.g., sapphire of diamond-like carbon transmissive to certain wavelengths of IR light), so that the eye tissue beneath the heat sink can be heated with absorbed light energy.

FIG. 5 illustrates a planned treatment zone 142 in the eye 100 of FIG. 4 for treating presbyopia, in accordance with embodiments. The planned treatment zone 142 can be disposed between an outer surface 144 (e.g., adjacent the conjunctiva 116) and inner surface 146 (e.g., adjacent the apex of the ciliary body 120 or a trabecular meshwork (not shown)) of the equatorial sclera region 134 of an eye 100. The equatorial sclera region 134 has an initial sclera thickness 148 defined by the distance between outer surface 144 and inner surface 146. The treatment can be applied by a laser to the treatment region 142 to heat and shrink and/or plasticize the mid-stroma of the equatorial sclera region 134, thereby causing the inner sclera surface 146 and inner ciliary body 120 to move in centrifugal directions 149a, 149b, while avoiding the conjunctiva 116 and ciliary muscles adjacent the ciliary body 120. The laser can be scanned through the sclera 102 posterior the limbus 150 such that limbal stem cells and insertions of the rectus muscles of the eye 100 are avoided.

FIG. 6 illustrates laser treatment of the eye 100 of FIG. 5 to treat presbyopia, in accordance with embodiments. The laser treatment can be applied to the treatment zone 142 to shrink and/or plasticize the tissue in the treatment zone 142 and thereby expand the CLS 130. Compared to the pre-treatment eye 100 of FIG. 5, the profile of the outer sclera surface 144 is substantially maintained (e.g., by stabilization as described herein), while the profile of the inner sclera surface 146 moves in a centrifugal direction 149a and is deflected substantially outward, resulting in a decreased sclera thickness 148 of the equatorial sclera region 134. The shrinkage of the mid-stroma causes the inner profile of the ciliary body 120 to move centrifugally outward toward the outer sclera surface 144, producing an increase in the size of the CLS 130 and an enhancement in the inward mobility of the ciliary body 120 during accommodation.

Figure 7:
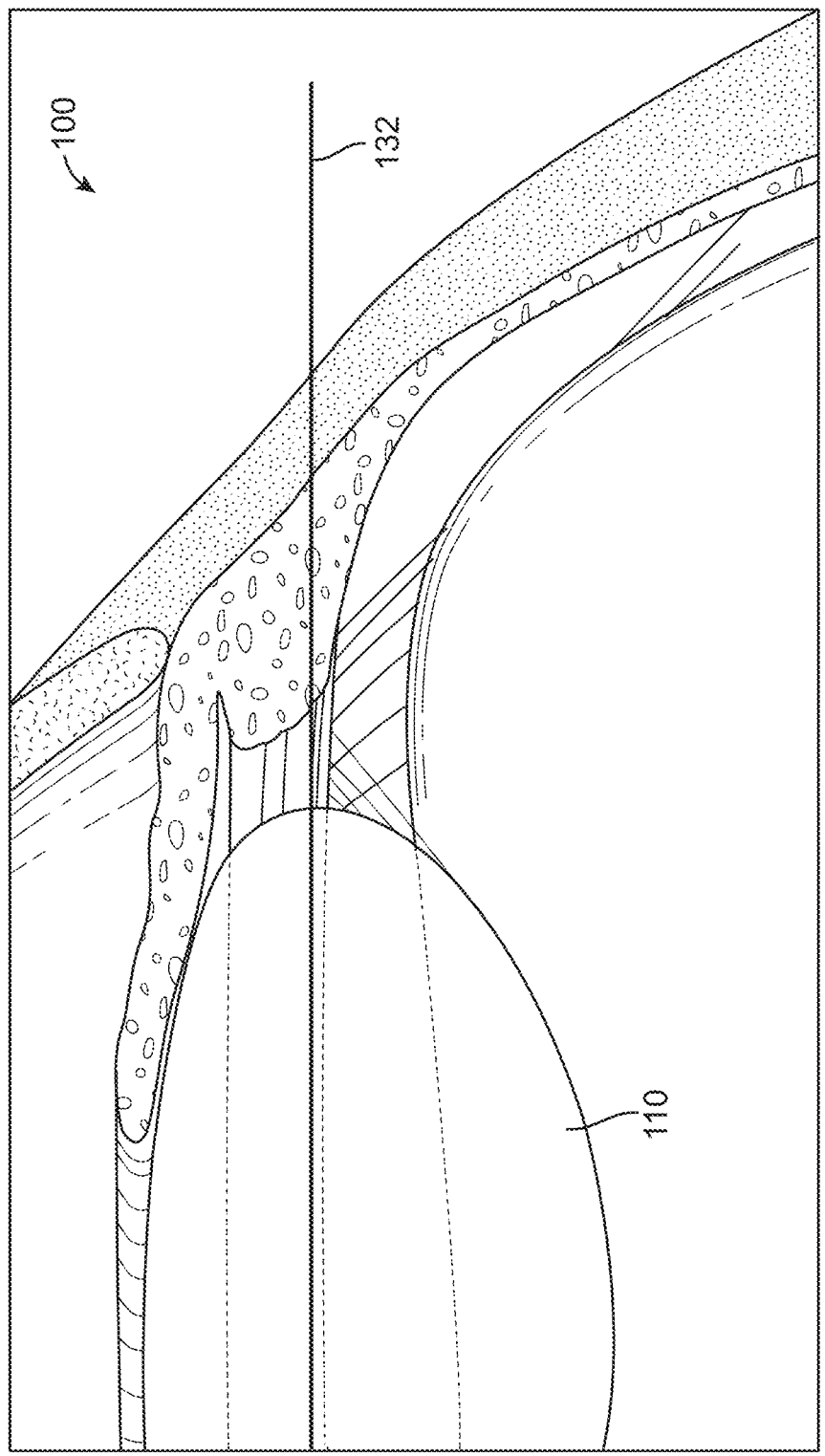
FIG. 7 illustrates the eye of FIG. 6 in a configuration for near vision, in accordance with embodiments.
Figure 8:
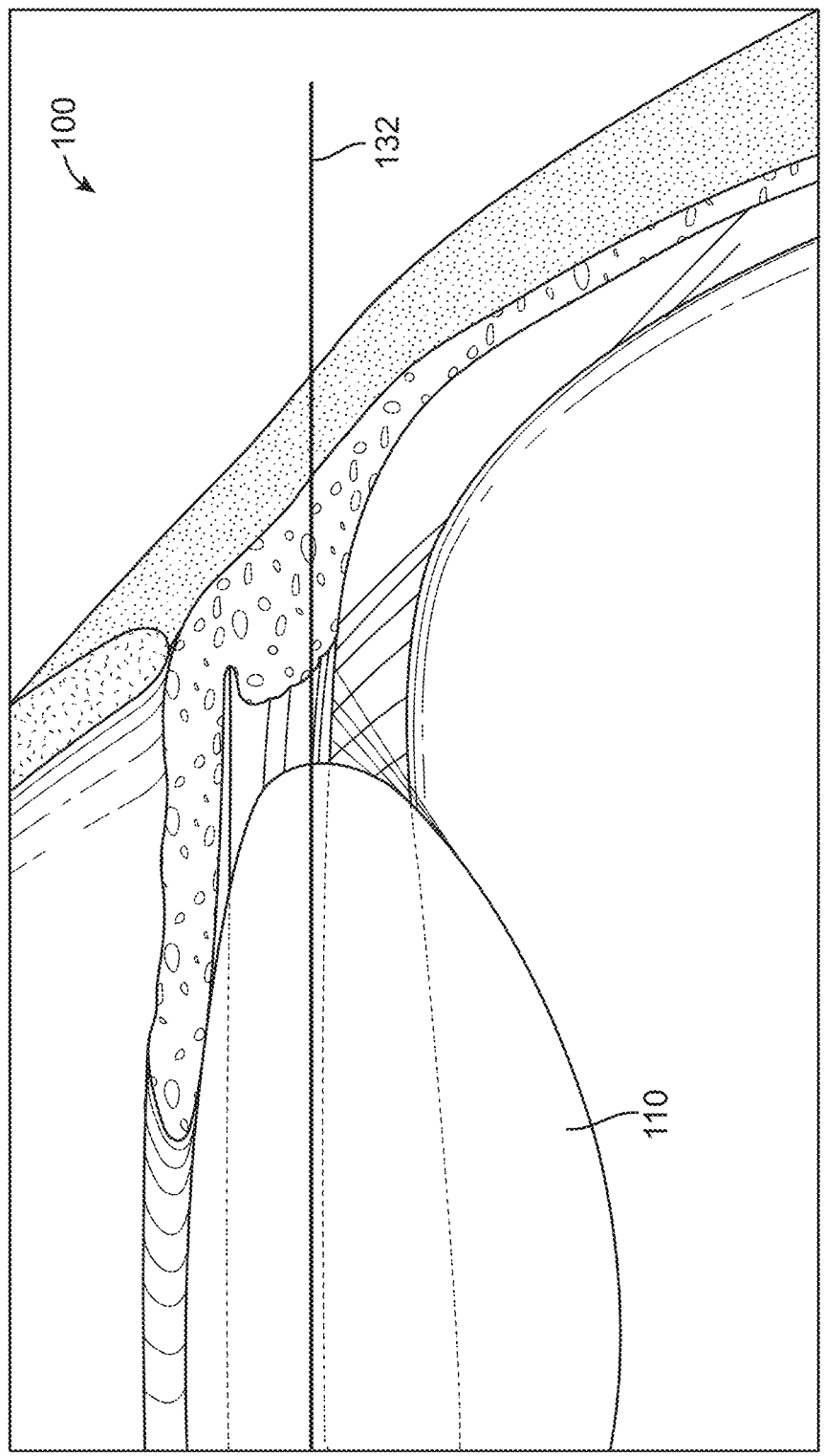
FIG. 8 illustrates the eye of FIG. 7 in a configuration for far vision, in accordance with embodiments.

Referring to FIGS. 7 and 8, an enhancement in centrifugal accommodative and un-accommodative movement of the eye 100 of FIG. 6 is observed following CLS expansion, in accordance with embodiments. FIG. 7 illustrates the post-operative eye 100 in a near vision configuration with the lens 110 in an accommodative state. FIG. 8 illustrates the post-operative eye 100 in a far vision configuration with the lens 110 in a un-accommodative state. Mobility of the ciliary body apex has been restored, and substantial changes in the curvature of the lens 110 and large accommodative amplitude along the lens equator plane 132 are observed, in contrast to the presbyopic eye of FIGS. 1 and 2.

Figure 9:
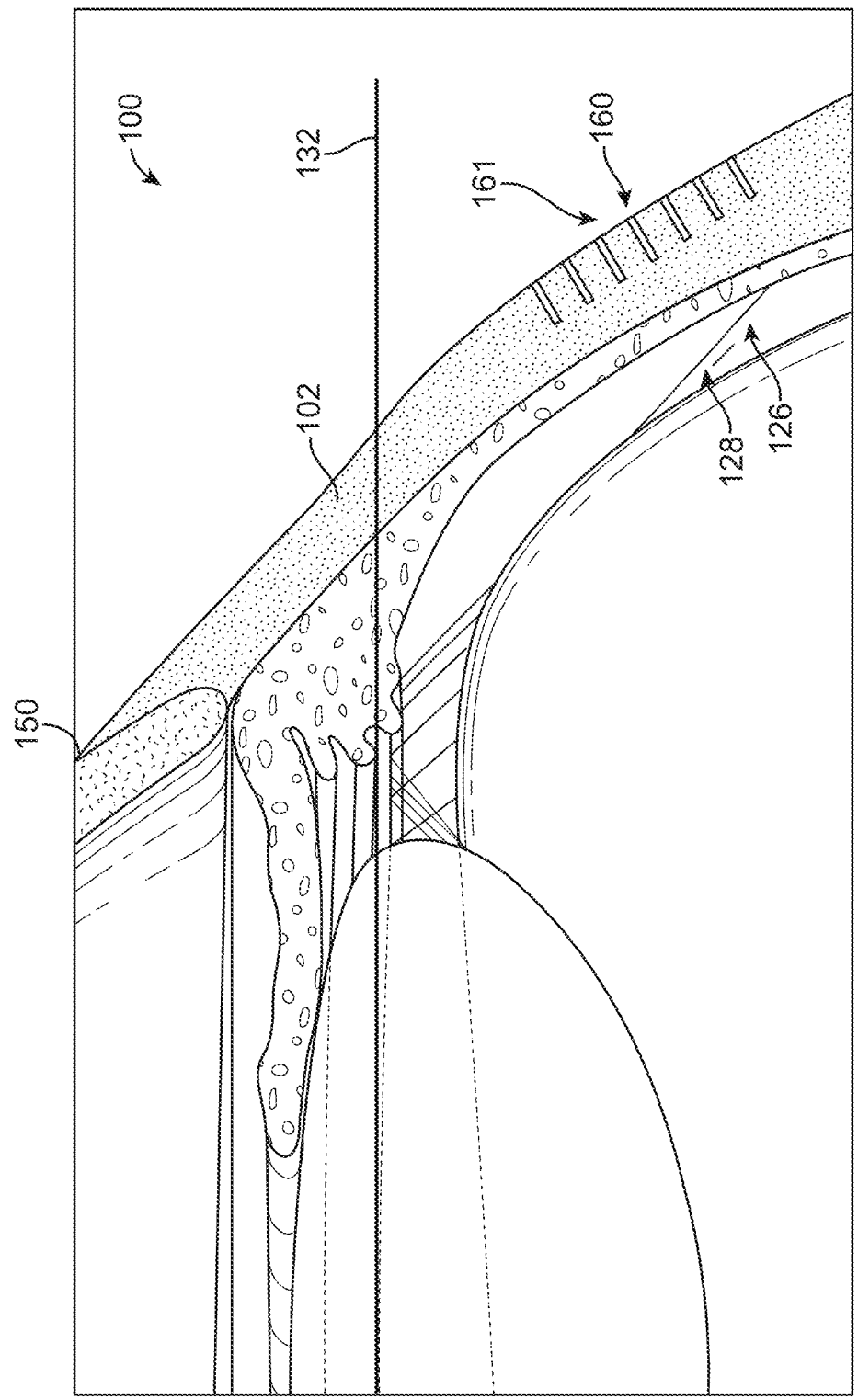
FIG. 9 illustrates laser softening of the insertion location of the posterior vitreal zonules of the eye of FIG. 8 to treat presbyopia, in accordance with embodiments.

FIG. 9 illustrates treatment of the eye 100 to soften the sclera proximate the insertion location of the PVZ 128 to treat presbyopia, in accordance with embodiments. The treatment region can extend posterior to the lens equator plane 132 and anterior to the insertion location of the PVZ 128 at the ora serrata 126. The treatment can be applied to the treatment region to ablate the tissue and form tiny fenestrations 160 within a scleral softening region 161 of the sclera 102. Alternatively or in combination, the tissue can be softened without ablation. In many embodiments, the PVZ insertion location can be softened order to enhance mobility of the PVZ and thereby increase the anterior mobility of the ciliary body apex during accommodation. Any suitable method can be used, such as laser-induced softening and/or plasticizing, to soften and/or plasticize any suitable portion of the sclera. The softening can include heating the portion of the sclera to a suitable temperature to weaken the tissue, such as within a range from about 70° C. to 90° C. The heat can be applied using energy, such as one or more of thermal energy, RF energy, electrical energy, microwave energy, or light energy. The energy may be emitted by the same energy source used to cross-link the eye or shrink and/or plasticize the inner portion of the eye, or by a different energy source. The softening and/or plasticizing treatment can be applied at any suitable location such that damage to non-treatment regions of the eye, such as muscles of the eye, is avoided. For example, the treatment can be applied to soften and/or plasticize four portions of the sclera, each corresponding to a location away from muscles of the eye including inferior muscles, superior muscles, nasal muscles, and temporal muscles. In many embodiments, after softening and/or plasticizing, the mobility of the PVZ 128 in accommodated and un-accommodated states is enhanced, and the anterior movement of the ciliary body apex is restored.

Figure 10:
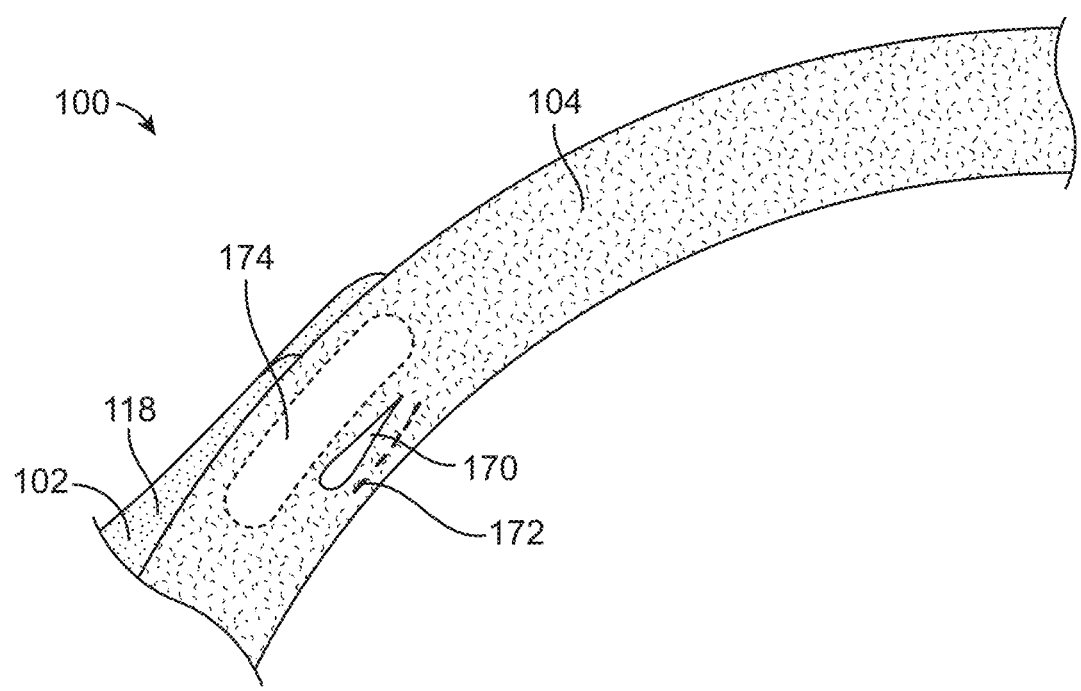
FIG. 10 illustrates a planned treatment to enhance corneal bending of the eye of FIG. 9 to treat presbyopia, in accordance with embodiments.
Figure 11:
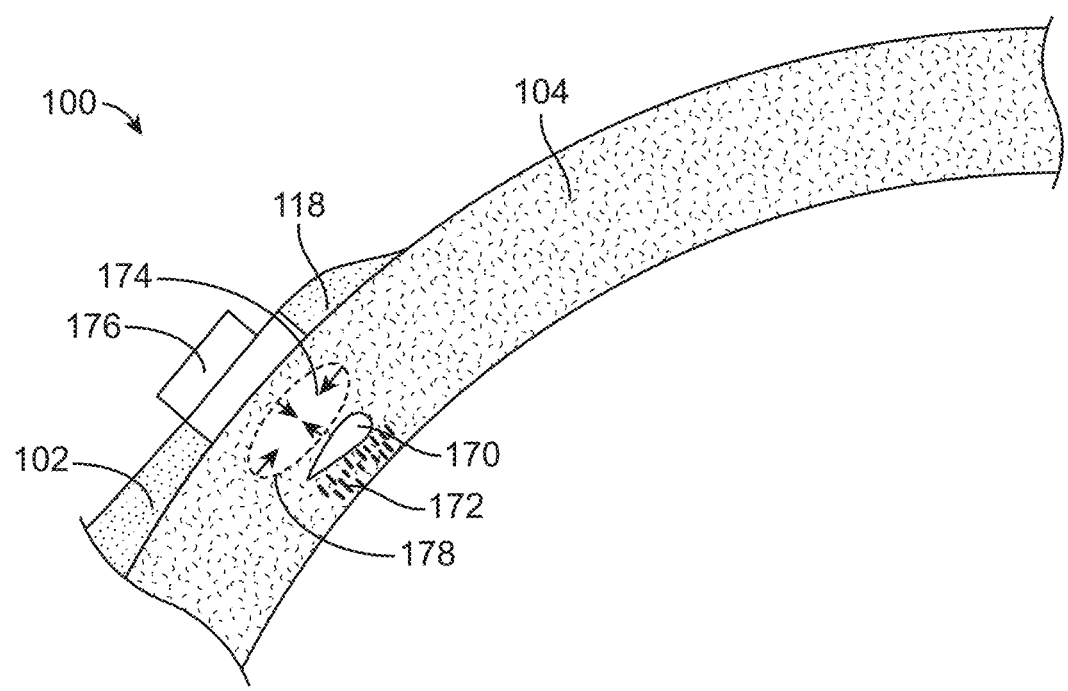
FIG. 11 illustrates a heat sink placed on the eye of FIG. 10 to enhance corneal bending to treat presbyopia, in accordance with embodiments.

FIGS. 10-11 illustrate aspects of a STEM treatment procedure to enhance corneal bending of the eye to treat presbyopia, or glaucoma, or both, in accordance with embodiments. In many embodiments, inner portions of the scleral spur and/or the cornea lateral to the Schlemm's canal and trabecular meshwork can be heated to increase the elasticity of the eye near the scleral spur inner portions, thereby enhancing corneal bending during accommodation to treat presbyopia, for example. For example, energy can be applied to shrink and/or plasticize the inner portions by heating the tissue to a suitable temperature without substantially weakening the tissue, such as within a range from about 50° C. to 70° C. Alternatively, energy can be applied to soften the inner portions by heating the tissue to a suitable temperature to weaken the tissue, such as within a range from about 70° C. to 90° C. Any suitable energy source can be used to enhance corneal bending, as described herein. The energy source can be the same energy source used to cross-link the eye or soften the PVZ insertion location, as described herein, or a different energy source, for example.

FIG. 10 illustrates a planned treatment of the eye 100 of FIG. 9 to soften the tissue lateral to the Schlemm's canal and trabecular meshwork to treat presbyopia, in accordance with embodiments. The Schlemm's canal 170 and trabecular meshwork 172 are positioned within the inner portion of the cornea 104 adjacent to the scleral spur 118 of the sclera 102. A planned treatment zone 174 can be disposed within the cornea 104 lateral to the Schlemm's canal 170, trabecular meshwork 172, and scleral spur 118. In many embodiments, the treatment zone 174 can be located outside the optically used portion of the cornea 104 (e.g., the peripheral corneal stroma). Alternatively or in combination, the treatment zone 174 can be located within a portion of the sclera 102 lateral to the Schlemm's canal 170 and trabecular meshwork 172, such as the scleral spur 118. The outer portion of the cornea 104 and/or the scleral spur 118 lateral to the planned treatment zone 174 can be cross-linked to create a stabilized outer profile, as previously described herein.

FIG. 11 illustrates a heat sink 176 placed on the eye 100 of FIG. 10 in order to shrink and/or plasticize the tissue lateral to the Schlemm's canal and trabecular meshwork to treat presbyopia, in accordance with embodiments. The heat sink 176 (e.g., a chilled sapphire window) can be placed on the scleral spur 118 to allow transmission of energy through the heat sink into the treatment zone 174 and avoid heating of the outer portion of the scleral spur 118, as previously described herein. Energy can be applied to the eye 100 at the treatment zone 174 in order to heat and shrink and/or plasticize the tissue as previously described herein, thereby creating a zone of shrinkage 178 within the cornea 104 lateral to the Schlemm's canal 170 and trabecular meshwork 172. The treatment can be applied to soften and increase the elasticity of the cornea 104 and/or scleral spur 118 such that corneal mobility and asphericity during accommodation is increased, thereby enhancing the accommodative power of the eye 100.

Additionally, in many embodiments, the shrinkage and/or plasticizing can move the tissue of the treatment zone 174 outward, thereby increasing the cross-sectional size of the Schlemm's canal 170 and/or channels of the trabecular meshwork 172. The expansion of the Schlemm's canal 170 and trabecular meshwork 172 can facilitate aqueous outflow of the eye 100, thereby normalizing the IOP. Accordingly, in many embodiments, the softening and/or plasticizing of the cornea 104 and/or scleral spur 118 lateral to the Schlemm's canal 170 and trabecular meshwork 172 as described herein can also be applied to treat glaucoma. The glaucoma treatment can be performed in combination with the presbyopia treatments described herein, or as a separate procedure.

Figure 12:
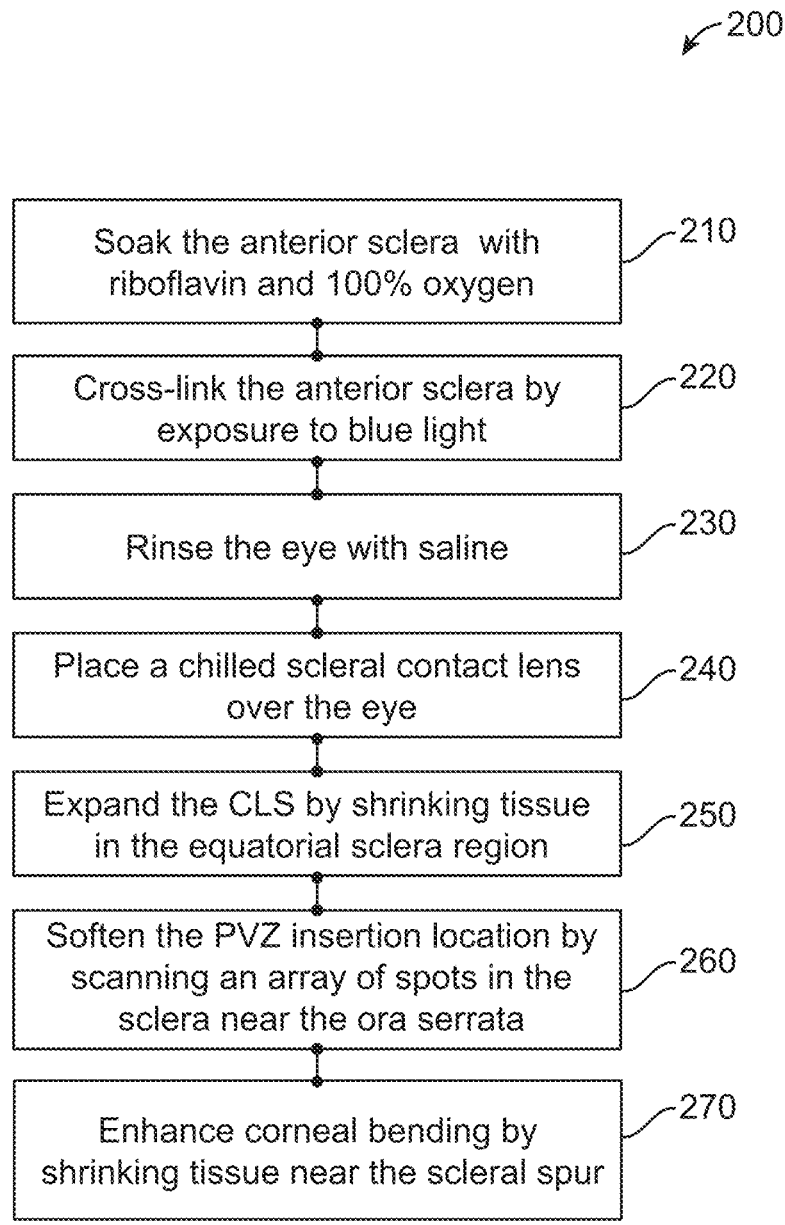
FIG. 12 is a simplified block diagram illustrating steps of a method to presbyopia, in accordance with embodiments.

FIG. 12 is a simplified block diagram depicting steps of a method 200 of treating an eye for presbyopia, in accordance with embodiments. Steps 210, 220, and 230 depict embodiments for stabilization of the anterior sclera, as previously described herein, for example. Steps 240 and 250 depict embodiments for expansion of the CLS, as previously described herein, for example. Step 260 depicts embodiments for softening of the PVZ insertion location, as previously described herein, for example. Step 270 depicts embodiments for enhancing corneal bending, as previously described herein, for example.

In step 210, the anterior sclera is soaked with riboflavin and 100% oxygen, for example. Although reference is made to 100% oxygen, the amount of oxygen applied to the eye can be less than 100% and often comprises an amount of oxygen greater than atmospheric oxygen, for example greater than about 20%. In many embodiments, the riboflavin is a 0.1 or 0.2% riboflavin solution. For example, IR laser-assisted conjunctival spotting can be used to soak the riboflavin into the anterior sclera for approximately 5 minutes. Alternatively or in combination, a microneedle array can be used to soak the riboflavin solution for approximately 10 minutes.

In step 220, the anterior sclera is exposed to blue light to cross-link the anterior sclera, as previously described herein. In many embodiments, the blue light is applied at an intensity of greater than 30 mW/cm$^2$. For example, the light can be applied at 50 mW/cm$^2$. The light can be applied for approximately 5 minutes in a suitable pattern. For example, a ring donut pattern with an inner diameter of 13 mm to 18 mm can be used in order to mask the cornea and limbus of the eye.

In step 230, the eye is rinsed with saline.

In step 240, a chilled scleral contact lens is placed over the eye to direct heat away from the outer portion of the eye, as previously described herein. The contact lens can be chilled to any suitable temperature, such as 4° C.

In step 250, the CLS is expanded by scanning an IR or mid-IR laser in the equatorial sclera region to cause thermal shrinkage and/or plasticizing of the tissue, as previously described herein. The laser can have any suitable emission wavelength, such as within a range of approximately 1.4 µm to 10 µm. In many embodiments, the laser emission wavelength can be one of the following: 1.48 µm, 1.54 µm, 2.01 µm, or 6.1 µm. Any suitable scanning pattern can be used, such as a continuous 360° circle around the eye, or discontinuous quadrant arcs (e.g., to avoid the insertion zones of the recti muscles). A finite element analysis of suitable portions of the eye (e.g., the ciliary body, lens, or vitreous zonules) can be used to determine a suitable scanning pattern. The scanning procedure can take approximately three to four minutes. In many embodiments, the laser can be scanned from 3 mm to 7 mm posterior to the limbus, to avoid limbal stem cells and recti, and is applied to the mid-stroma of the sclera only, to avoid the epithelium, conjunctiva, and ciliary muscles. The mid-stroma of the sclera can be heated to approximately 60° C. to increase scleral elasticity and shrink and/or plasticize the mid-stroma within a range of 100 µm to 250 µm of shrinkage, and thereby increase the ciliary apex ring diameter by approximately 400 µm and the size of the CLS within a range of 200 µm to 500 µm. The inward mobility of the ciliary body can be enhanced post-treatment by approximately 250 µm.

In step 260, the PVZ insertion location is softened and/or plasticized by scanning an array of spots is scanned in the sclera near the ora serrata with an IR or mid-IR laser, as previously described herein. The laser can be any suitable laser with any suitable emission wavelength, as described herein. Any suitable scanning pattern can be used, such as discontinuous quadrant arcs (e.g., to avoid the recti muscles). The scanning procedure can take approximately three to four minutes. In many embodiments, each spot in the array has a diameter ranging from 50 µm to 1 mm in diameter. For example, each spot can have a 100 µm spot diameter and approximately 250 µm sclera depth. The spots can form tiny fenestrations of approximately 50% sclera depth in the treatment region. The array can be scanned 3 mm to 7 mm posterior to the limbus (e.g., between the ora serrata and the anterior ciliary body). The softening and/or plasticizing can be applied such that excessive bleeding and coagulation of surface conjunctiva blood vessels is avoided. In many embodiments, PVZ mobility and anterior ciliary body apex movement is enhanced post-treatment by approximately 1 mm.

In step 270, corneal bending is enhanced by scanning an IR or mid-IR laser is scanned near the scleral spur to cause thermal shrinkage, as previously described herein. The laser can be any suitable laser with any suitable emission wavelength, as described herein. Any suitable scanning pattern can be used, such as a continuous 360° circle around the eye, or discontinuous quadrant arcs (e.g., to avoid the insertion zones of the recti muscles). The scanning procedure can take approximately one minute.

Although the above steps show method 200 of treating an eye in accordance with embodiments, a person of ordinary skill in the art will recognize many variations based on the teaching described herein. Some of the steps may comprise sub-steps. Many of the steps may be repeated as often as beneficial to the treatment. One or more steps of the method 200 may be performed with any suitable eye treatment system, such as the embodiments described herein. Some of the steps may be optional, such as one or more of steps 210, 220, or 230. The order of the steps can be varied. For example, steps 250, 260, and 270 may be performed in any suitable order.

The processor of the treatment apparatus as disclosed herein can be configured with one or more instructions to perform the method 200 and/or any one of the steps and sub-steps of the method 200. The processor may comprise memory having instructions to perform the method, and the processor may comprise a processor system configured to perform the method for example. In many embodiments the processor comprises array logic such as programmable array logic (hereinafter PAL), configured to perform one or more steps of the method 200, for example.

Figure 13:
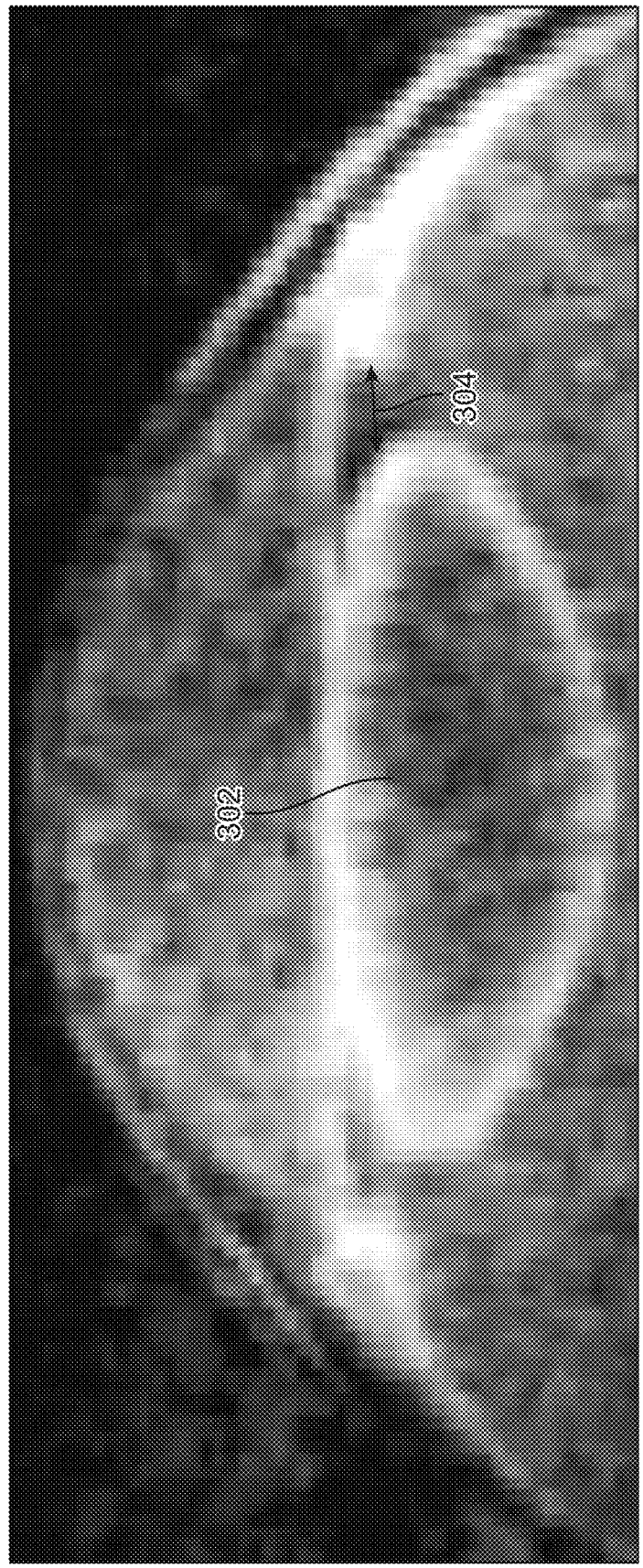
FIG. 13 illustrates a magnetic resonance image (hereinafter "MRI") of a non-presbyopic eye in a far vision configuration, in accordance with embodiments.

FIG. 13 illustrates a MRI of a non-presbyopic eye 300 in a far vision configuration, in accordance with embodiments. The lens 302 is in an un-accommodative state and exhibits a flattened shape. The eye 300 has a relatively increased CLS 304 compared to the near vision configuration, described below.

Figure 14:
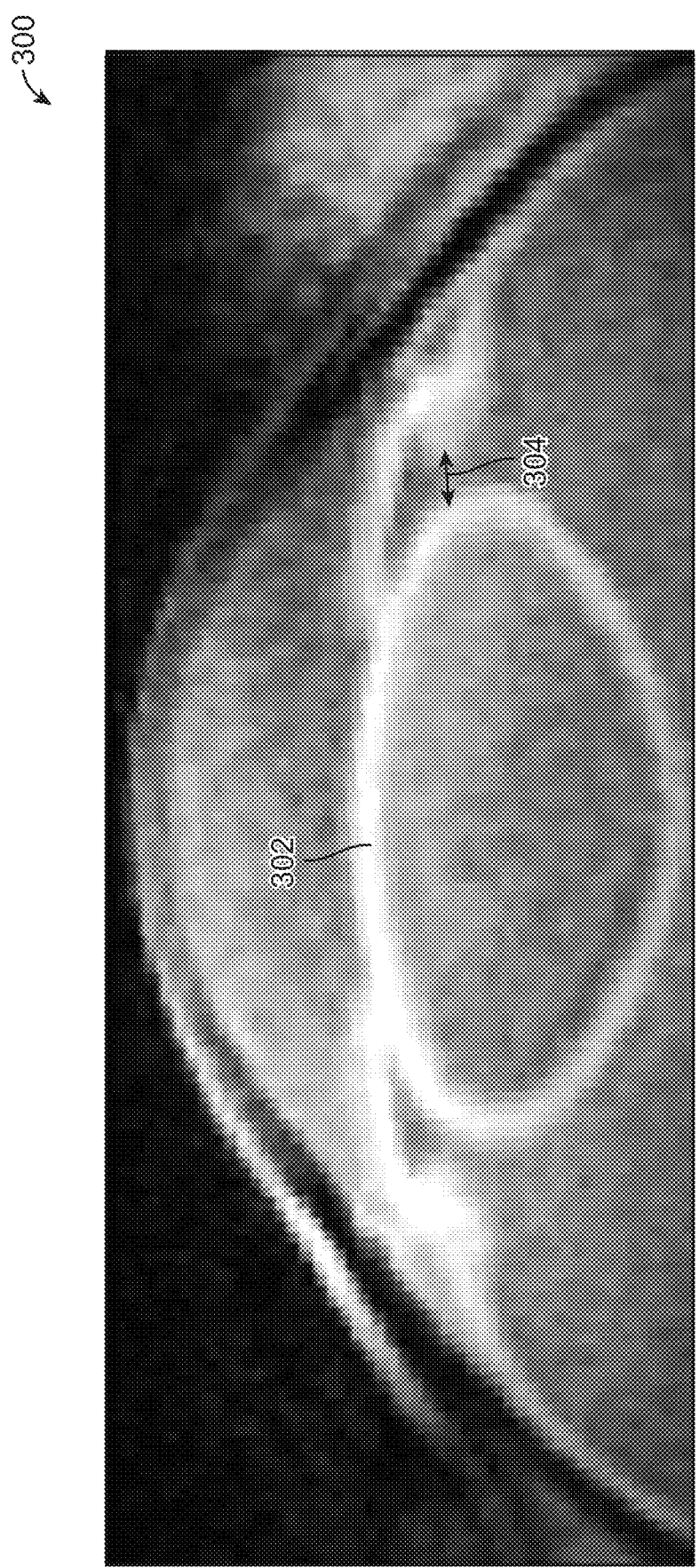
FIG. 14 illustrates a MRI of a non-presbyopic eye in a near vision configuration, in accordance with embodiments.

FIG. 14 illustrates a MRI of a non-presbyopic eye 300 in a near vision configuration, in accordance with embodiments. The lens 302 is in an accommodative state and exhibits significant changes in curvature and location compared to the far vision configuration of FIG. 13. The CLS 304 is reduced compared to the near vision configuration of FIG. 13.

Figure 15:
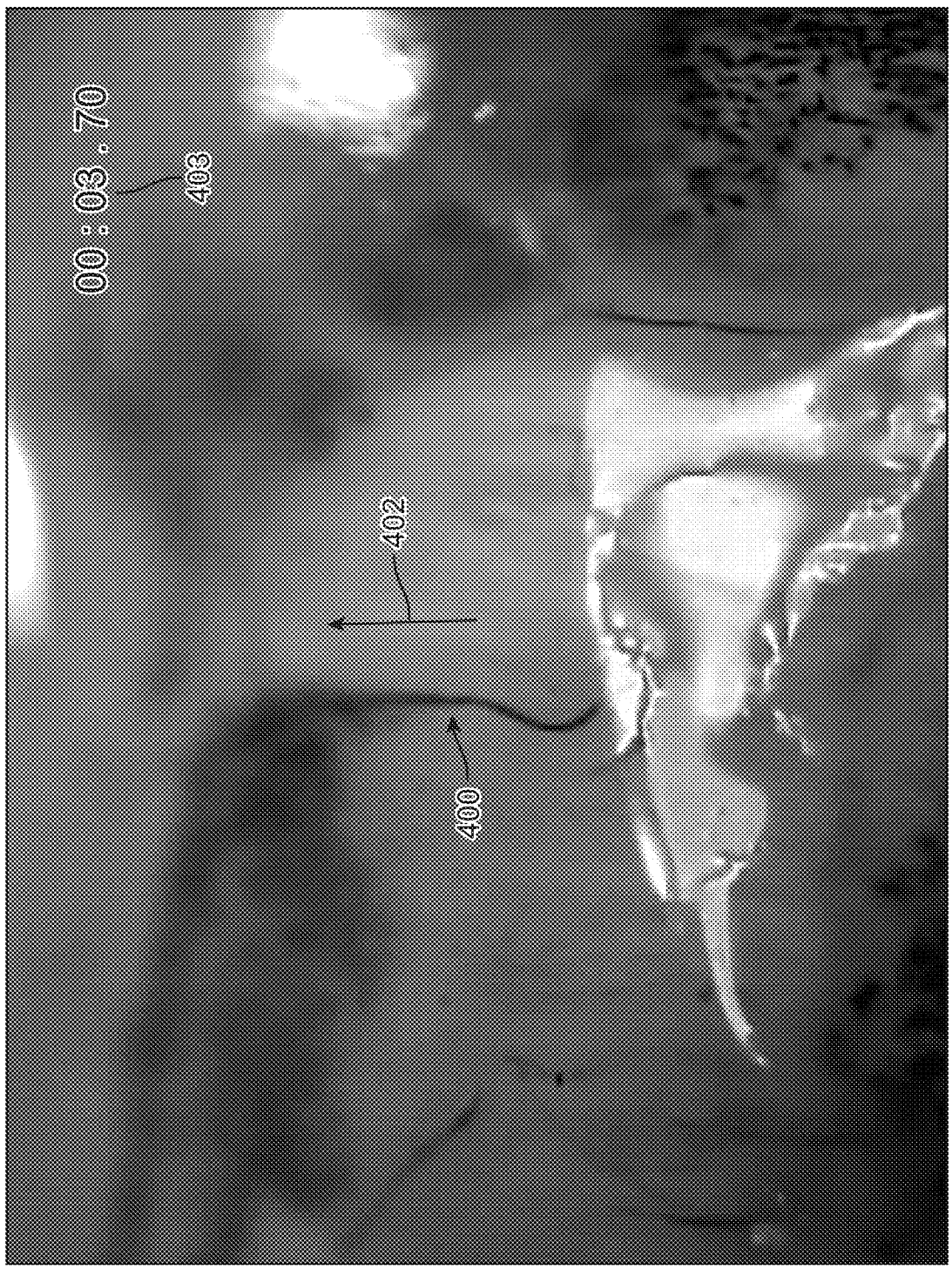
FIG. 15 illustrates a video image of laser treatment to shrink scleral tissue, in accordance with embodiments.

FIG. 15 illustrates a video image of laser treatment to shrink scleral tissue, in accordance with embodiments. A laser is applied to the tissue to cause the marker vessel and local tissue 400 to shrink and migrate in the direction indicated by arrow 402 at an initial time 403.

Figure 16:
FIG. 16 illustrates the video image of FIG. 15 at a later time point during application of laser treatment, in accordance with embodiments.

FIG. 16 illustrates the video image of FIG. 15 at a later time 403, in accordance with embodiments. Laser irradiation is applied at subsurface treatment spot 404. The marker vessel and local tissue 400 have shrunk and migrated towards the treatment spot 404 along direction 402.

Figure 17:
FIG. 17 illustrates the video image of FIG. 16 at a later time point, in accordance with embodiments.

FIG. 17 illustrates the video image of FIG. 17 at a later time 403, in accordance with embodiments. The marker vessel and local tissue 400 continue to shrink and migrate towards treatment spot 404.

Figure 18:
FIG. 18 illustrates the video image of FIG. 17 at a later time point showing involution of the marker vessel and tissue into the laser treatment spot, in accordance with embodiments.

FIG. 18 illustrates the video image of FIG. 17 at a later time 403 showing involution of the marker vessel and tissue 400 into the laser irradiation treatment spot 404, in accordance with embodiments.

Based on the teachings disclosed herein, a person of ordinary skill in the art can configure the treatment energy to shrink the inner portion as described herein.

Figure 19:
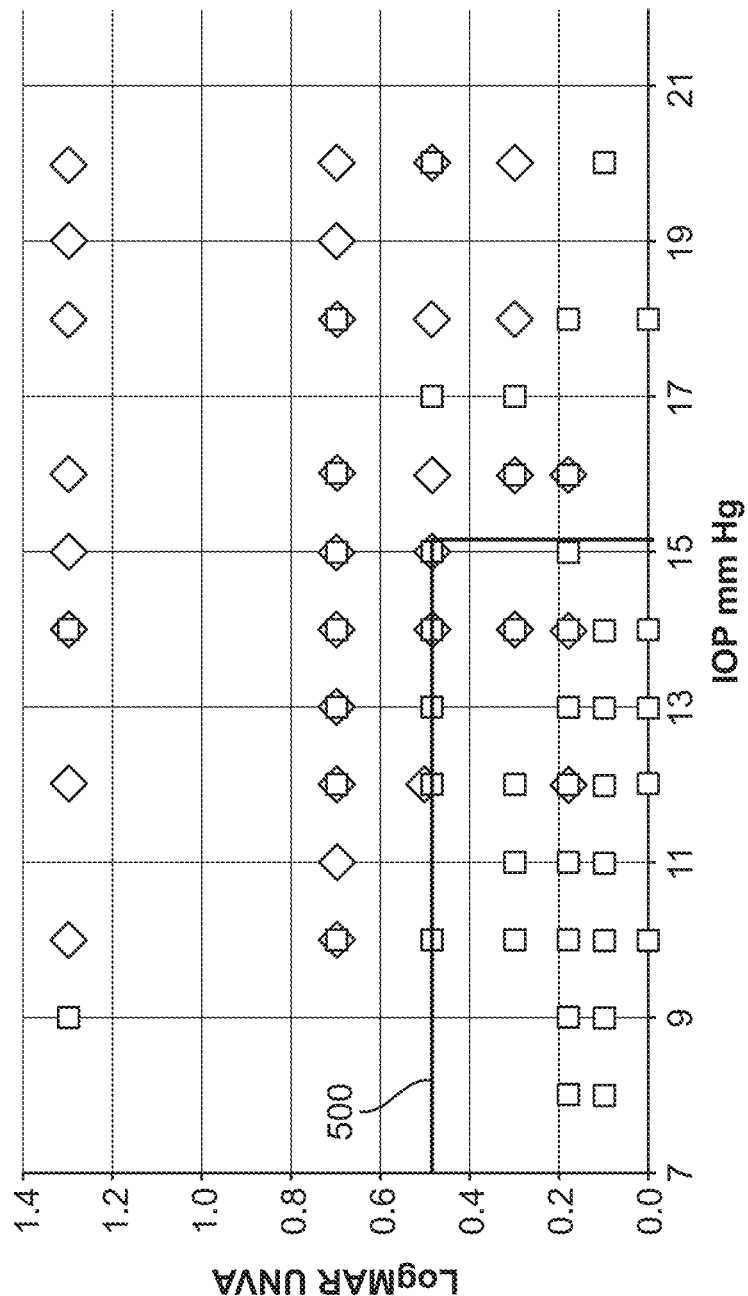
FIG. 19 illustrates a plot of uncorrected near visual acuity (hereinafter "UNVA") versus IOP, in accordance with embodiments.

FIG. 19 illustrates a plot of UNVA versus TOP for patients pre- and post-STEM treatment, in accordance with embodiments. The UNVA is represented by a logarithm of the minimal angle of resolution (hereinafter "log MAR") for UNVA. Pre-STEM treatment data points are represented by diamonds. Post-STEM treatment data points are from a one year follow-up after the STEM procedure as described herein was performed and are represented by squares. Post-STEM patients exhibit reduced TOP values compared to pre-STEM patients. UNVA is also improved in post-STEM patients, as indicated by lower log MAR UNVA values compare to pre-STEM patients. A significant number of post-STEM patients have TOP values of 15 mm Hg or less, and visual acuity score of Jaeger 4 (hereinafter "J4") or better, as indicated by the data points lying on and within the boundary 500.

Figure 20:
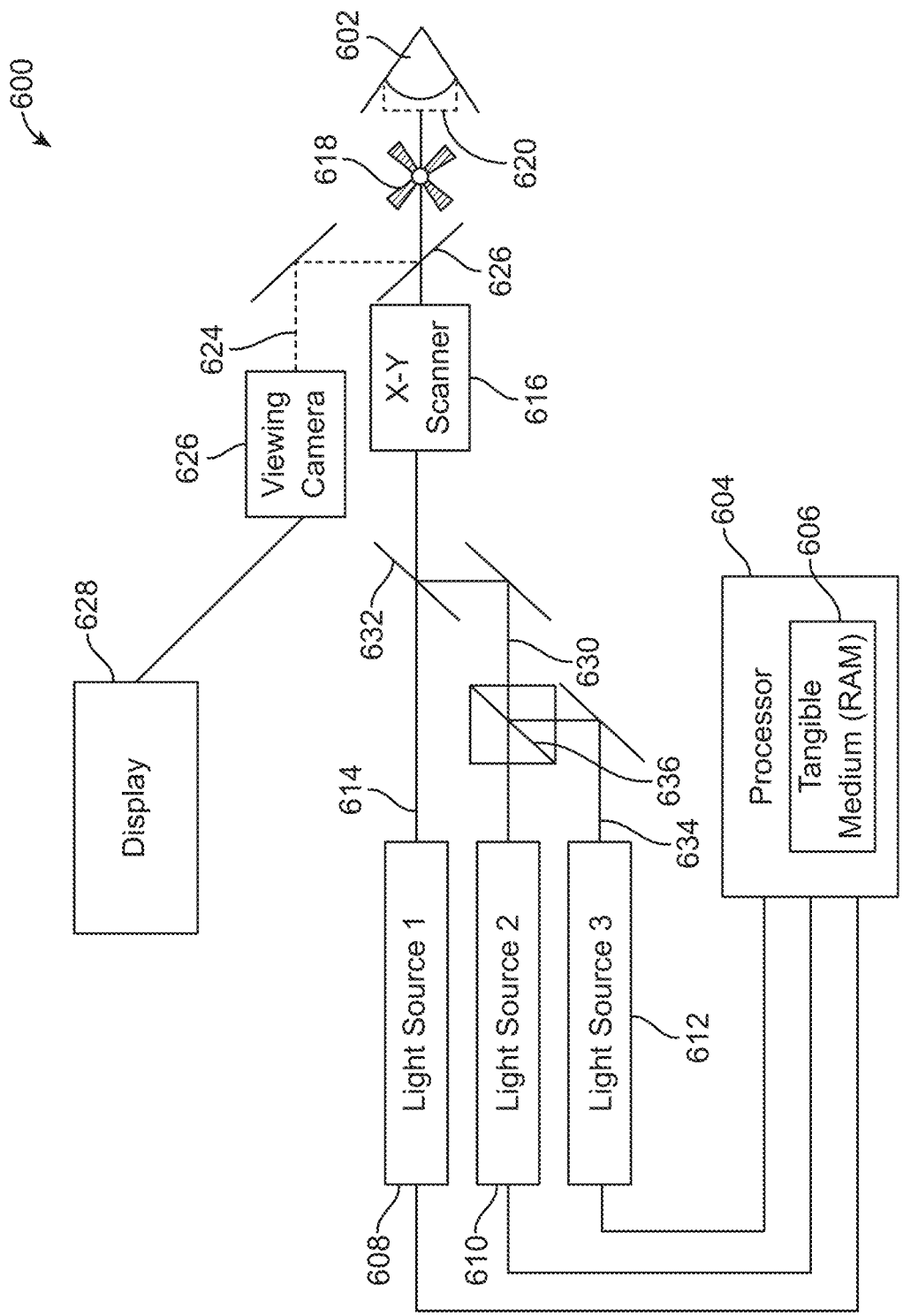
FIG. 20 illustrates a system for treating an eye, in accordance with embodiments.

FIG. 20 illustrates a system 600 for treating an eye 602, in accordance with embodiments. The system 600 includes a processor 604 having a tangible medium 606 (e.g., a RAM). The processor 604 is operatively coupled to a first light source 608, a second light source 610, and a third light source 612. The first light source 608 emits a first beam of light 614 that is scanned by X-Y scanner 616 through an optional mask 618 and optional heat sink 620 onto the eye 602. The mirror 622 directs light energy from the eye 602 to a viewing camera 626 coupled to a display 628. An independent non-treatment light source for the viewing camera can be provided, for example. The mirror 622 may direct a portion of the light beam returning from eye 602 to the camera 626, for example. The second light source 610 emits a second beam of light 630 that is combined by a first beam combiner 632 with the first beam of light 614 prior to passing through X-Y scanner 616. The third light source 612 emits a third beam of light 634 that is combined by a second beam combiner 636 with the second beam of light 630 prior to passing through the first beam combiner 632.

In many embodiments, the beams of light 614, 630, and 634 can be scanned onto the eye 602 at a specified X and Y position by the X-Y scanner 616 to treat the eye 602. The X-Y scanner can be configured to scan the combined light beams onto the eye 602 in a suitable treatment scan pattern, as previously described herein. An optional mask 618 can be used to mask the light applied to the eye 602, for example, to protect masked portions of the eye 602 while treating other portions as described herein. An optional heat sink 620 can be placed on the eye 602 during treatment to avoid heating specified portions of the eye 602, as previously described herein.

The system 600 can be used to apply light energy to the eye 602 in accordance with any suitable treatment procedure, such as the embodiments described herein. In many embodiments, the first light beam 614 has a first wavelength, the second light beam 630 has a second wavelength, and the third light beam 634 has a third wavelength. Each wavelength can be a different wavelength of light. Alternatively, at least some of the wavelengths can be the same. For example, in accordance with the embodiments described herein, the first light beam 614 can have a wavelength suitable to: cross-link an outer portion of the eye 602 and shrink an inner portion of the eye 602; shrink the inner portion and cross-link the outer portion concurrently; shrink the inner portion after the outer portion has been cross-linked; or any suitable combinations thereof. Alternatively, the first light beam 614 can have a first wavelength suitable to cross-link the outer portion of the eye 602, as previously described herein, and the second light beam 630 can have a second wavelength suitable to shrink the inner portion of the eye 602, as previously described herein. The third light beam 634 can have a third wavelength suitable to soften a portion of the sclera of the eye 602, as previously described herein. Any suitable combination of wavelengths of light for applying any combination of the treatments described herein, concurrently or separately, can be used.

Figure 21:
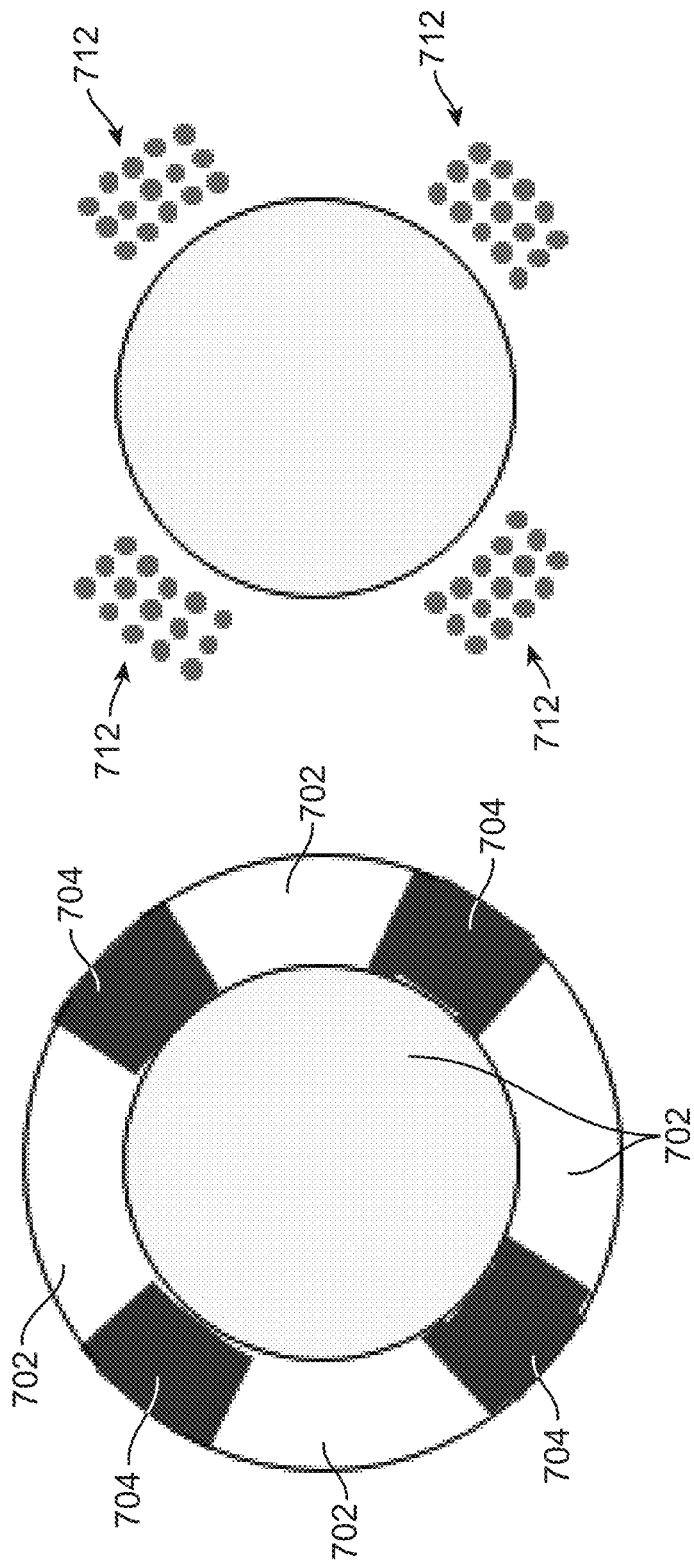
FIGS. 21A and 21B show a mask pattern and a treatment scan pattern for treating an eye, respectively, in accordance with embodiments.

FIGS. 21A and 21B illustrate mask pattern 700 and treatment scan pattern 710, respectively, suitable for combination with the treatments described herein, in accordance with embodiments. Any suitable system can be used to apply the mask pattern 700 and treatment scan pattern 710, such as the treatment system 600. For example, mask pattern 700 and treatment scan pattern 710 can be used to selectively soften portions of the sclera, such as in step 260 of method 200. The mask pattern 700 can be applied to the eye by any suitable mask, such as the optional mask 618 of system 600. The mask pattern 700 can be used to protect portions of the eye under masked regions 702 and allow softening of portions of the eye under transmissive regions 704, as previously described herein. The treatment scan pattern 710 can be applied by any suitable system, such as by the system 600 using X-Y scanner 616. The treatment scan pattern 710 can be used to form four quadrants of laser spots 712 on the sclera to soften the sclera, as previously described herein.

Figure 22:
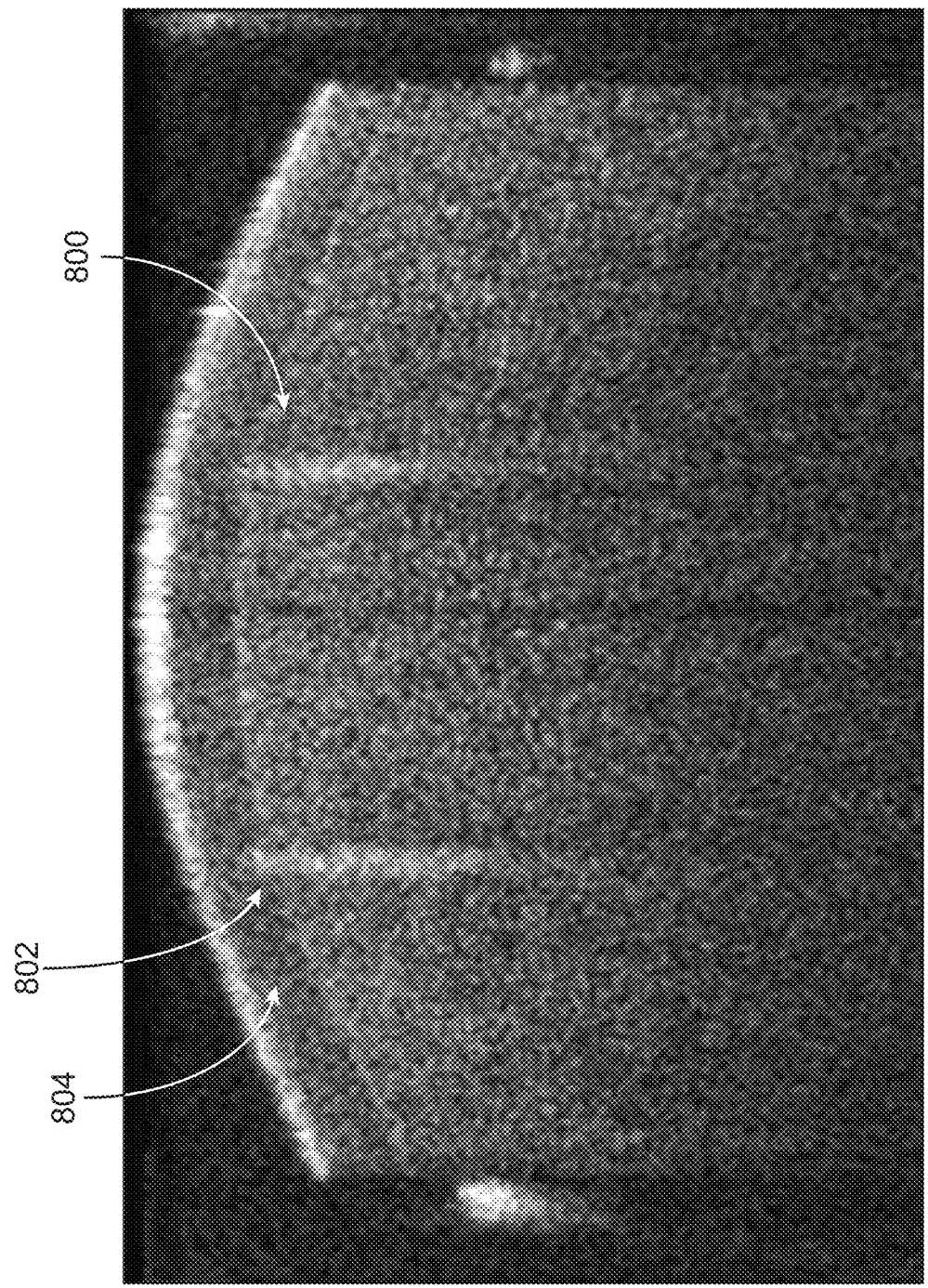
FIG. 22 illustrates an optical coherence tomography (hereinafter "OCT") image of a subsurface laser treatment of cornea, in accordance with embodiments.

FIG. 22 illustrates an OCT image of a subsurface laser treatment of a cornea 800 suitable for combination with the treatments described herein, in accordance with embodiments. The cornea 800 includes the Bowman's membrane 802. Subsurface laser treatment (e.g., using a medium intensity laser) is applied to the treatment regions 804 posterior to the Bowman's membrane 802, such that subsurface shrinkage of the corneal tissue at treatment regions 804 occurs. The subsurface shrinkage can be used to reshape (e.g., flatten) the cornea 800 and the Bowman's membrane 802 to treat the eye.

Figure 23B:
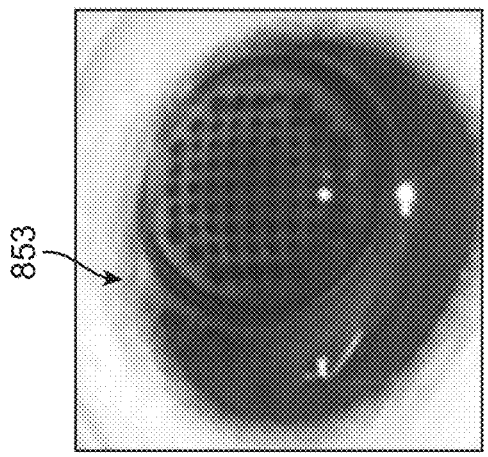
FIG. 23B illustrates an image of the fluorescein stain pattern of the eye of FIG. 23A, in accordance with embodiments.
Figure 23D:
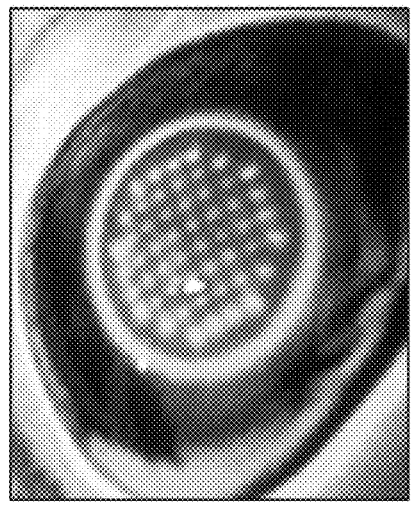
FIG. 23D illustrates a fluorescence image of the eye of FIG. 23A, in accordance with embodiments.
Figure 23A:
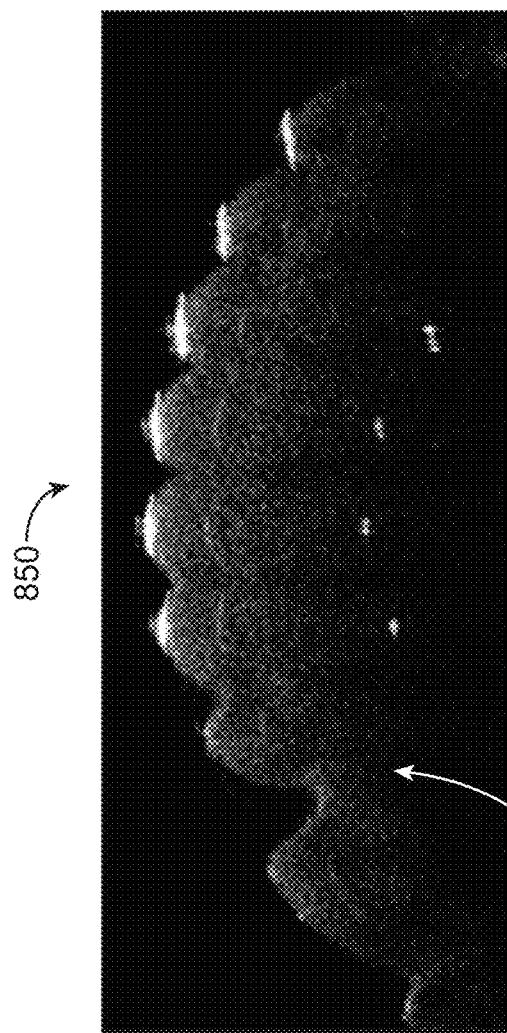
FIG. 23A illustrates an OCT image of a cornea of an eye treated with a hollow microelectrode array, in accordance with embodiments.
Figure 23C:
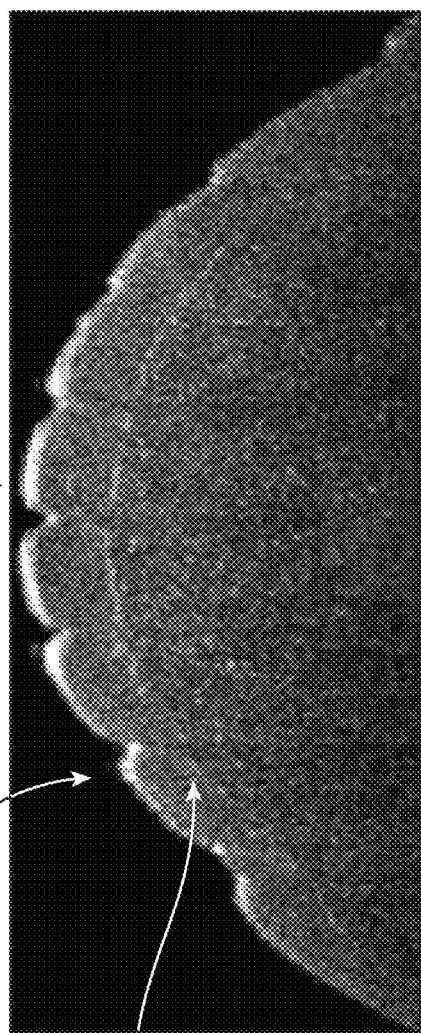
FIG. 23C illustrates an OCT image of the cornea of FIG. 23A with increased grey levels, in accordance with embodiments.

FIGS. 23A-D illustrate images of a cornea 850 of an eye treated with a hollow microelectrode array suitable for combination with the treatments described herein, in accordance with embodiments. FIG. 23A illustrates an OCT image of the cornea 850 including the Bowman's membrane 852. FIG. 23B illustrates an image of the fluorescein stain pattern 853 of the eye of FIG. 23A. FIG. 23C illustrates an OCT image of the cornea 852 as in FIG. 23A with increased grey levels. FIG. 23D illustrates a fluorescence image of the eye of FIG. 23A. The hollow microelectrode array can be applied to the cornea to produce a patterned corneal shrinkage profile such as the corneal shrinkage profile 854. For example, in many embodiments, the hollow microelectrode array can be used to apply energy (e.g., light energy) to a cross-linking agent (e.g., a chemical photosensitizer such as riboflavin) in order to stabilize selected portions of the cornea (e.g., through collagen cross-linking) to maintain a desired corneal surface profile. Any suitable method and cross-linking agent previously described herein in the context of cross-linking of the sclera can be used to cross-link the cornea.

Figure 24A:
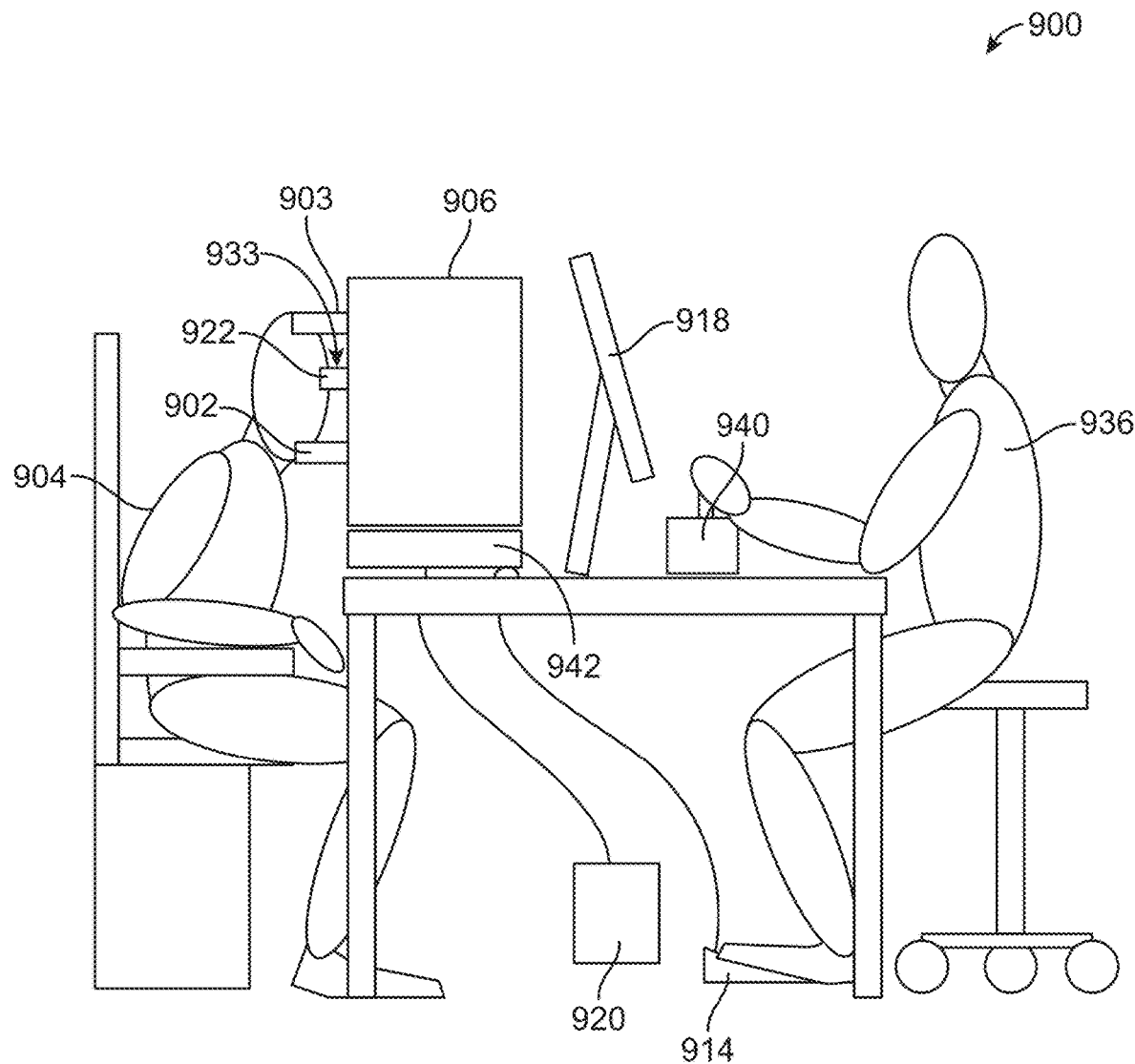
FIGS. 24A and 24B show a treatment apparatus, in accordance with embodiments.
Figure 24B:
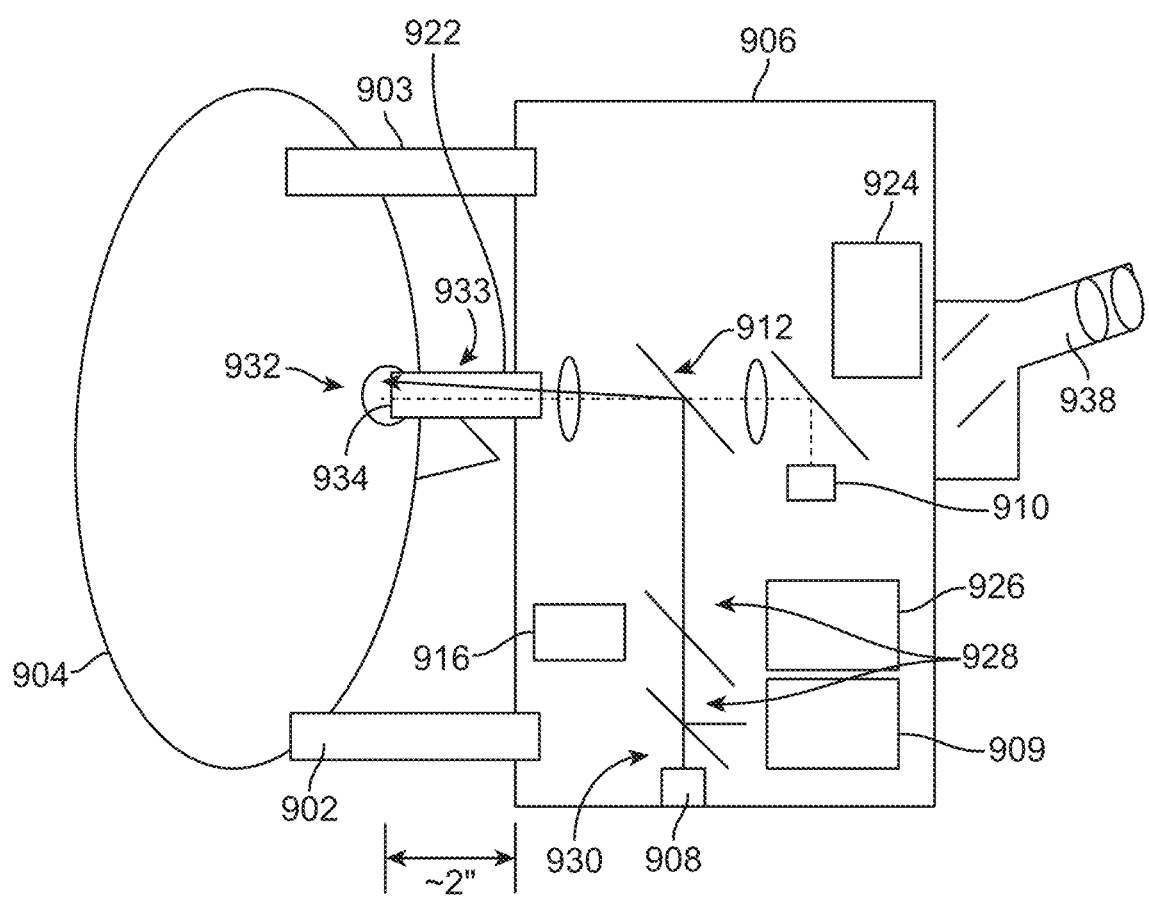

FIGS. 24A and 24B show a treatment apparatus 900, in accordance with embodiments. The apparatus 900 comprises one or more components as described herein and configured to perform treatment as described herein, and can be combined in one or more of many ways in accordance with embodiments described herein, for example with reference to one or more components of FIG. 20. The treatment apparatus 900 comprises a chin rest 902 and head rest 903 to support the head of the patient 904. The laser delivery system 906 comprises a treatment energy source such as an infrared laser source 908, an alignment laser 909 such as a visible laser, a fixation light 910 such as an LED, a scanner 912, a foot switch 914, an energy detector 916, a computer display monitor 918, a chiller 920, a cooling lens assembly 922, and a camera 924 coupled to a processor 926. The processor comprises one or more instructions of a treatment program embodied on a tangible medium such as a computer memory or a gate array in order to execute one or more steps of a treatment method as disclosed herein.

The treatment apparatus 900 comprises a laser delivery system 906 to treat the patient. Beam splitters 928 can be provided along the optical path to align the infrared laser beam 930 from the infrared laser 908 with the alignment laser beam from the alignment laser 909, such that the treatment beam extends coaxially with the visible alignment beam toward an eye 932 engaged with the docking station 933. A scanner 912 can be provided to scan the laser beam 930 in a desired pattern on the eye 932 as disclosed herein. A temperature sensor 934 can be coupled to the processor 926 and the cooling lens assembly 922 to allow treatment when the cooling lens assembly 922 comprises a temperature to cool the conjunctiva as disclosed herein. The detector 916 can measure the energy of the treatment energy beam in order to adjust the laser beam energy to provide a treatment to the eye 932 as disclosed herein. The patient 904 can view the fixation LED 910 in order to align the eye 932. The visible camera 924 can be coupled to the processor 926 to display an image of the eye 932 to a user 936 (e.g., a surgeon), for example with a real time display on monitor 918. Alternatively or in combination, the user 936 can view the eye 932 with eye pieces 938 of an operating microscope, for example.

The laser system 906 comprises components coupled to the processor 926 and the processor 926 comprises instructions to treat the patient 904 in accordance with embodiments described herein. The laser 908 is coupled to a foot pedal 914 for the operator 936 to treat the eye 932 with the laser beam 930. A joystick 940 can be coupled to a X,Y,Z stage 942 of a slit lamp base to position the laser and imaging system in relation to the patient 904. Alternatively or in combination, the joystick 940 can be coupled to the scanning optical system to direct the treatment to a desired location of the eye 932. The processor 926 comprises instructions to scan the laser beam 930 with an intensity on the eye 932 to provide softening of the stroma as described herein.

Figure 25A:
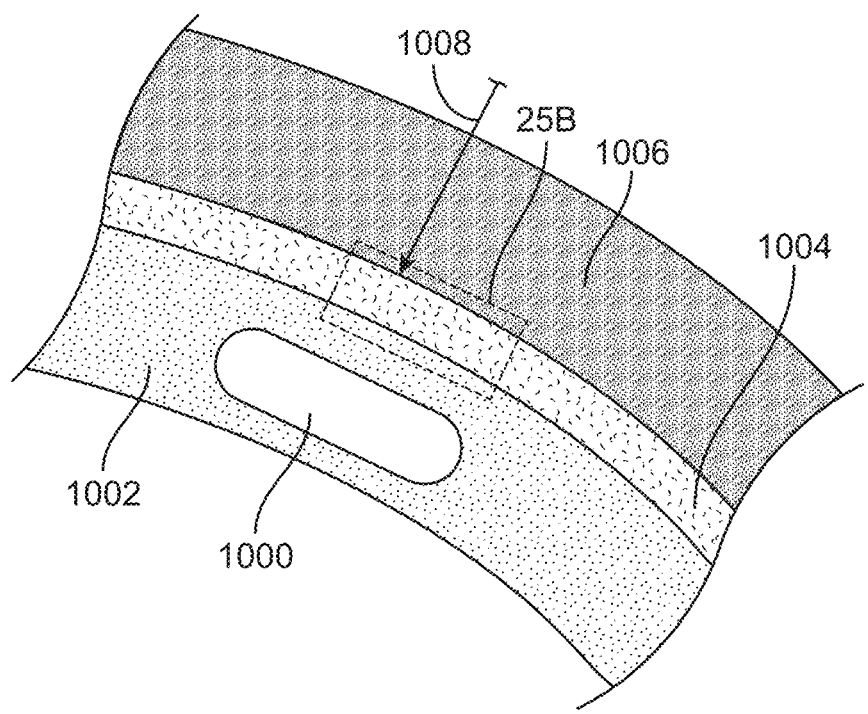
FIG. 25A shows a treatment region of the sclera and conjunctiva under a heat sink comprising a cooling lens contacting the conjunctiva.

FIG. 25A shows a treatment region 1000 of the sclera 1002 and conjunctiva 1004 under a heat sink comprising a cooling lens 1006 contacting the conjunctiva 1004. The cooling lens structure 1006 can provide one or more intact layers of epithelium 1003 above the conjunctiva 1004 and treatment zone 1000 when tissue has been relocated as described herein, in order to provide presbyopia and or glaucoma treatment and to inhibit regression of effect. Maintaining one or more layers of epithelium 1003 can provide improved an improved protective barrier function of the eye. The cooling lens structure 1006 comprises a material that is optically transmissive to the one or more wavelengths of light used to heat and soften the scleral tissue. The treatment laser beam 1008 can be transmitted through the cooling structure 1006 such that the treatment laser beam 1008 irradiates an upper surface of the epithelium 1003 of the conjunctiva 1004, and the epithelium 1003 of the conjunctiva 1004 may comprise a lower basal cell layer, an intermediate wing cell layer and an upper squamous layer. In many embodiments, these layers of the epithelium 1003 transmit a sufficient amount of energy of the treatment beam to provide at least partial penetration of the laser beam into the scleral tissue of the eye.

Figure 25B:
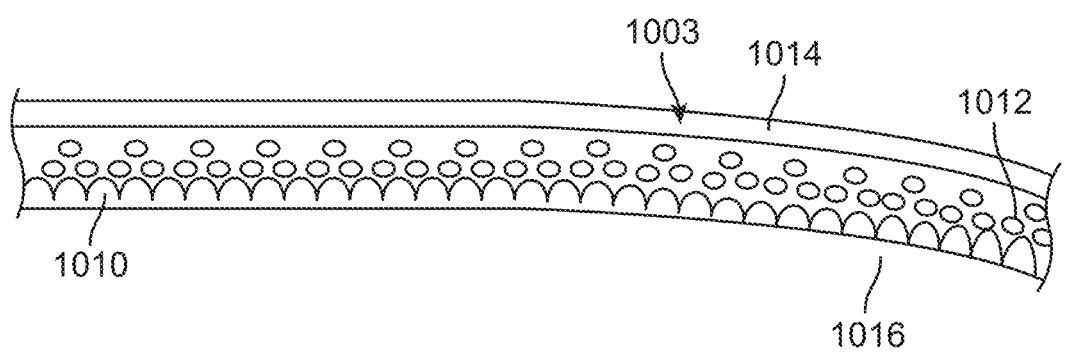
FIG. 25B shows a region of the conjunctiva above the scleral softening treatment region as in 25A comprising an intact epithelial layer subsequent to delivery of laser energy with the optically transmissive heat sink contacting the tissue.

FIG. 25B shows a region of the conjunctiva 1004 above the scleral softening treatment region as in 25A comprising an intact epithelial layer 1003 subsequent to delivery of laser energy with the optically transmissive heat sink contacting the tissue. One or more layers of the epithelium 1003 above the conjunctival stroma 1016 such as one or more of the basal 1010, wing 1012, or squamous 1014 layers of epithelium 1003 remains intact over at least a portion of the treatment zone to provide improved comfort and retained efficacy of treatment in many embodiments.

Figure 26A:
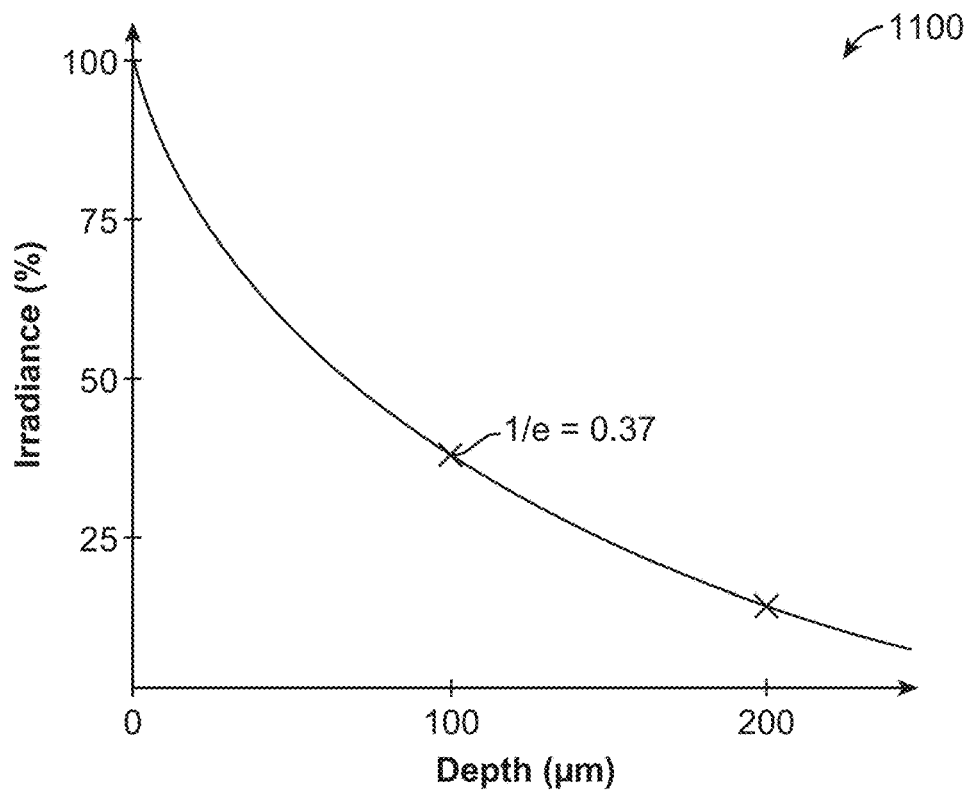
FIG. 26A shows a tissue depth penetration of a laser beam, in accordance with embodiments.

FIG. 26A shows a tissue depth penetration profile 1100 of a laser beam. In many embodiments, the laser beam comprises a tissue absorbance such that the 1/e depth is about 100 micrometers (um). The percentage irradiance of the tissue decreases exponentially from about 100% near the outer surface tissue to about 37% (1/e) at a distance within the conjunctiva of the tissue, for example at a distance of about 100 um from the surface of the conjunctiva. In many embodiments, greater than half of the electromagnetic energy of the laser beam is absorbed with the conjunctiva, and the scleral stroma comprises a treatment temperature greater than the conjunctiva. While the laser beam may comprise one or more of many wavelengths as described herein, in many embodiments the laser beam comprises an infrared laser beam such as an infrared laser beam having a wavelength of about 6.1 um, for example.

Figure 26B:
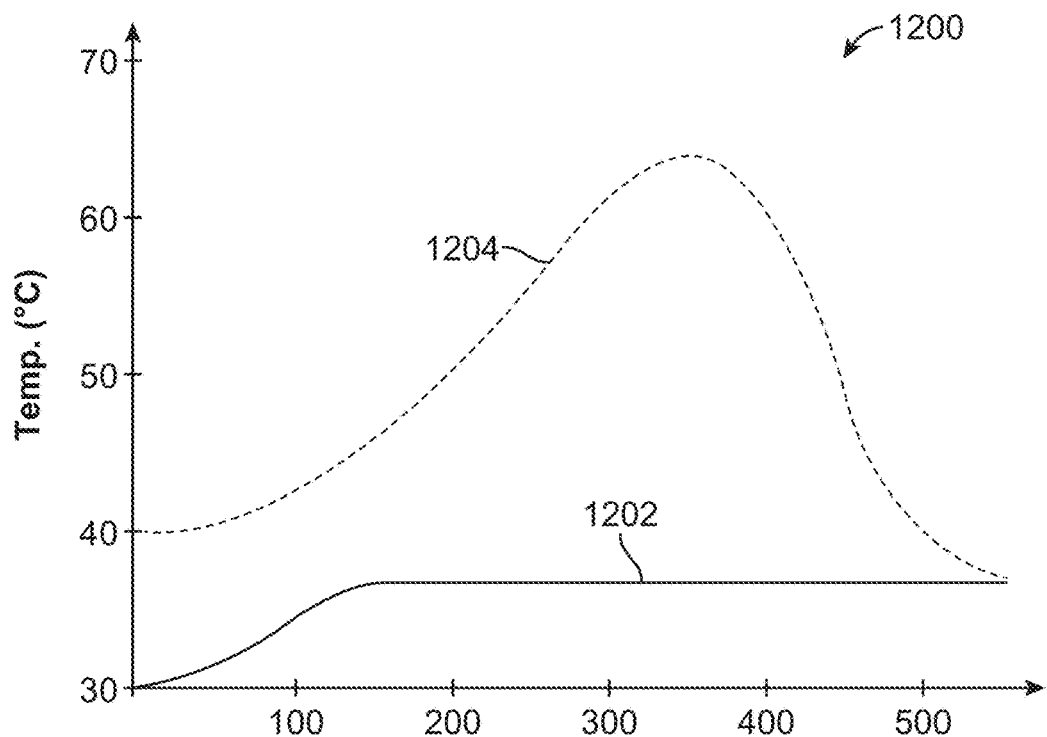
FIG. 26B shows a tissue heating profile with scanning of a laser beam as in FIG. 26A, in accordance with embodiments.

FIG. 26B shows a tissue heating profile 1200 with scanning of a laser beam as in FIG. 26A, including initial and treatment curves 1202, 1204. The temperature of the outer surface of the eye can be decreased with one or more of a heat sink or cooling, for example. The outer surface of the eye can be cooled to a desired temperature with the contact cooling structure, and the eye treated. The chilled heat sink structure can be chilled to a temperature within a range from above the freezing temperature of saline at about −3 degrees Celsius (C.) to below ambient room temperature of about 20 degrees Celsius. Alternatively, a heat sink can be provided without chilling. Alternatively, a heat sink can be provided without chilling, for example when the ambient temperature comprises about 20 degrees C. The eye can be treated with the scanning laser beam comprising a tissue absorption profile as shown in FIG. 26A, in order to provide softening of the scleral tissue at a depth. As heat can be conducted away from the conjunctiva with the heat sink, the inner portion of the eye comprising the scleral stroma comprises a temperature greater than the outer conjunctiva. The depth profile of the heating of the eye can be controlled to inhibit damage to the ciliary body and choroid when the scleral stroma is softened as described herein.

The treatment temperature profiles of FIGS. 26A and 26B can be used in combination with tissue treatment patterns as disclosed herein, and the treatment profiles can be used to treat presbyopia, or glaucoma, or both for example. For example, the treatment profiles can be used in combination with reference to FIGS. 9 and 21B, and the softened tissue of the sclera can extend a majority of the distance from the sclera of the lens equator plane to the scleral location proximate the ora serrata corresponding to the insertion of the posterior vitreous zonules as described herein. In many embodiments, the scleral softening region comprises a majority of the distance between the lens equator and the ora serrata in each of the plurality of four quadrants of treatment. The scleral softening region extending the majority of the distance can be located closer to the ora serrata than the plane of the lens equator, for example.

The sclera can be softened as described herein in one or more of many ways in order to encourage movement of the posterior vitreous zonules at least anteriorly in order to provide improved accommodation, such as with one or more of light energy, ultrasound energy, electrical energy, heating, electroporation or optoporation, for example. The softening may include micro needle arrays (hereinafter "MNAs") for adjunct drug delivery following or before canal or trabecular meshwork expanding scleral translocation elastomodulation (STEM), for example. Alternatively or in combination photonic desincrustation or galvanic desincrustation can be used to remove stiff scleral tissue structures or molecules, for example. In some embodiments, photoporation can be used in accordance with embodiments disclosed herein. These alternative energy sources and tissue treatments are suitable for combination in accordance with embodiments disclosed herein and can be used to provide scleral softening to treat presbyopia or glaucoma, or both, for example.

Although reference is made to softening scleral tissue with cross-linking, in many embodiments the scleral softening can be performed without cross-linking to treat one or more of presbyopia or glaucoma.

Although reference has been made to trans-conjunctival treatment of the sclera with energy delivery through the conjunctiva, in some embodiments the conjunctiva can be incised to provide access to the scleral tissue and treatment of the scleral tissue with energy in accordance with embodiments disclosed herein.

Figure 27A:
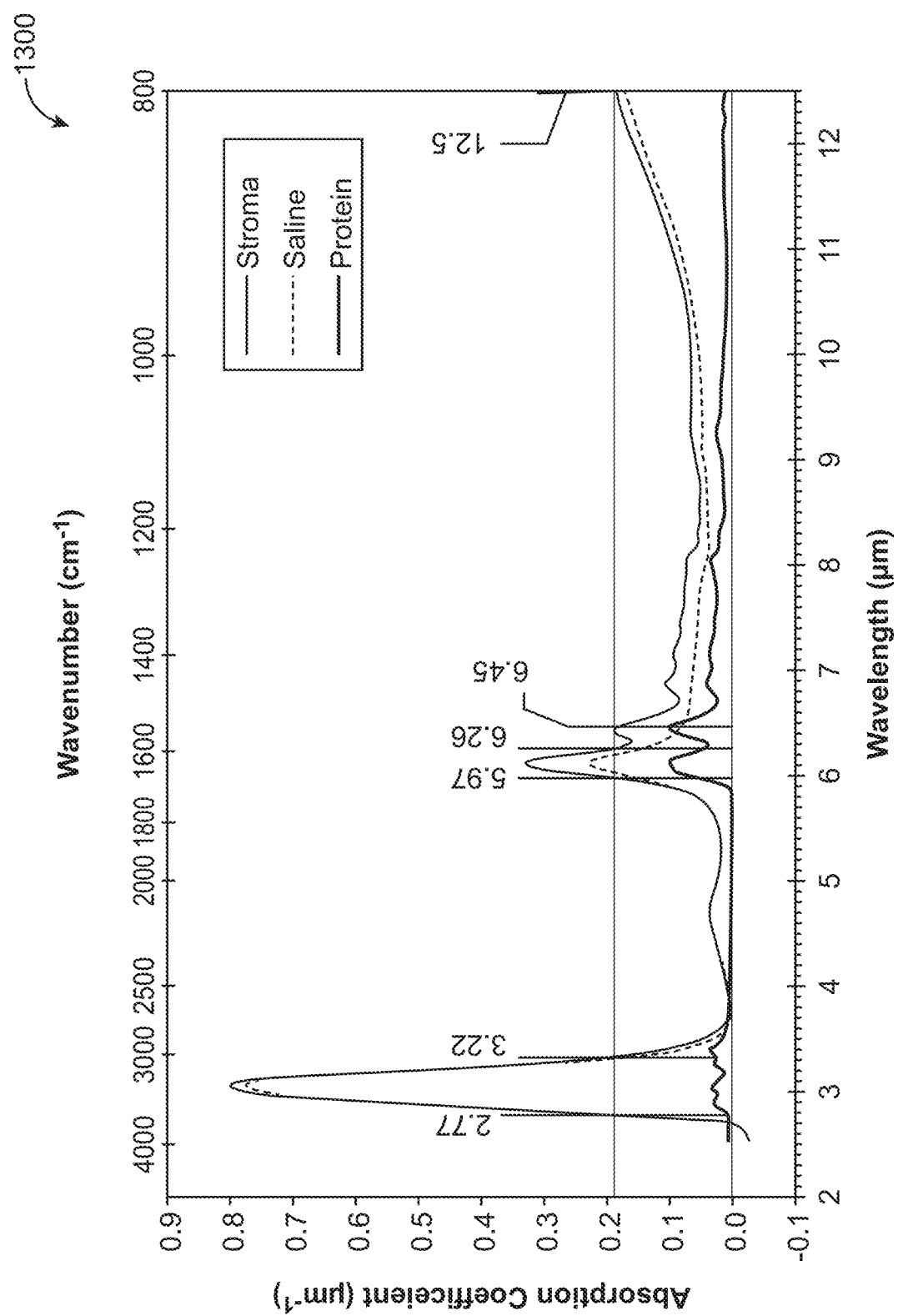
FIG. 27A shows absorbance spectra, suitable for incorporation in accordance with embodiments.

FIG. 27A shows absorbance spectra 1300. The absorbance spectra show the absorbance of corneal stroma and stromal components saline and protein, in which the protein comprises collagen. A first absorbance peak appears at about 3 um wavelength, stroma and saline have a very strong absorbance of about 0.8 per um of tissue, and the protein comprising collagen is much lower. A second absorbance peak appears at about a 6.1 um wavelength, and a third at about a 6.5 um wavelength. The absorbance of stroma of about 0.3 per um of tissue is stronger than the absorbance of saline of about 0.22 per um of tissue, both of which are stronger than the absorbance of protein of about 0.06 per micron of tissue. The relatively stronger absorbance ratio of stroma and collagen to saline at about 6 um as compared to absorbance ratios of stroma and collagen to saline at about 3 um can provide an improve tissue treatment. The absorbance spectra show stroma having a higher absorbance than saline at a wavelength of about 6 um. The higher absorbance of saline at about 6 um can be suitable for treatment in accordance with embodiments disclosed herein, and can provide an improved delivery of laser energy to the stroma.

Figure 27B:
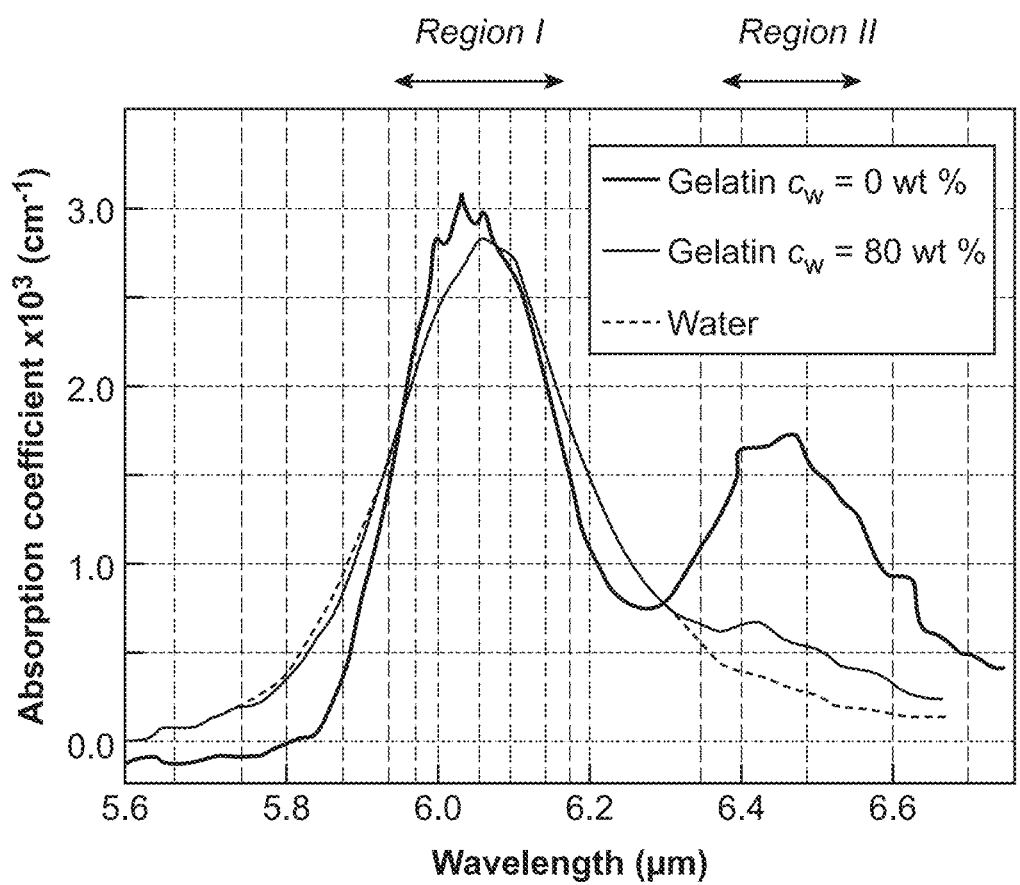
FIG. 27B shows absorbance spectra in accordance with embodiments.

FIG. 27B shows absorbance spectra in accordance with embodiments. The absorbance spectra show the absorbance of water, gelatin with a water concentration of zero (Cw=0) and gelatin with a water concentration of 80 percent by weight (Cw=80). At about 6 um, both gelatins and water have similar absorbance of about 3000 per cm (0.3 per um). At about 6.4-6.5 um, gelatin with Cw=0 has an absorbance of about 1500 per cm, gelatin with Cw=80 has an absorbance of 500 per um and water has an absorbance of about 400 per um.

Gelatin comprises substantial amounts of collagen and may comprise a material suitable for modeling absorbance of ocular tissue such as the stroma, sclera, cornea and conjunctiva, for example.

In many embodiments, the wavelength of light used to irradiate tissue comprises a substantial amount of absorption of non-water components of the eye such as protein, glycoprotein and nutrients, for example. In many embodiments, the non-water components of the eye comprise at least about 10% of the absorbance, for example at least about 20% of the absorbance, for example 30%, 40%, 50%, or more of the absorbance, in order to provide tissue softening, for example.

Figure 28:
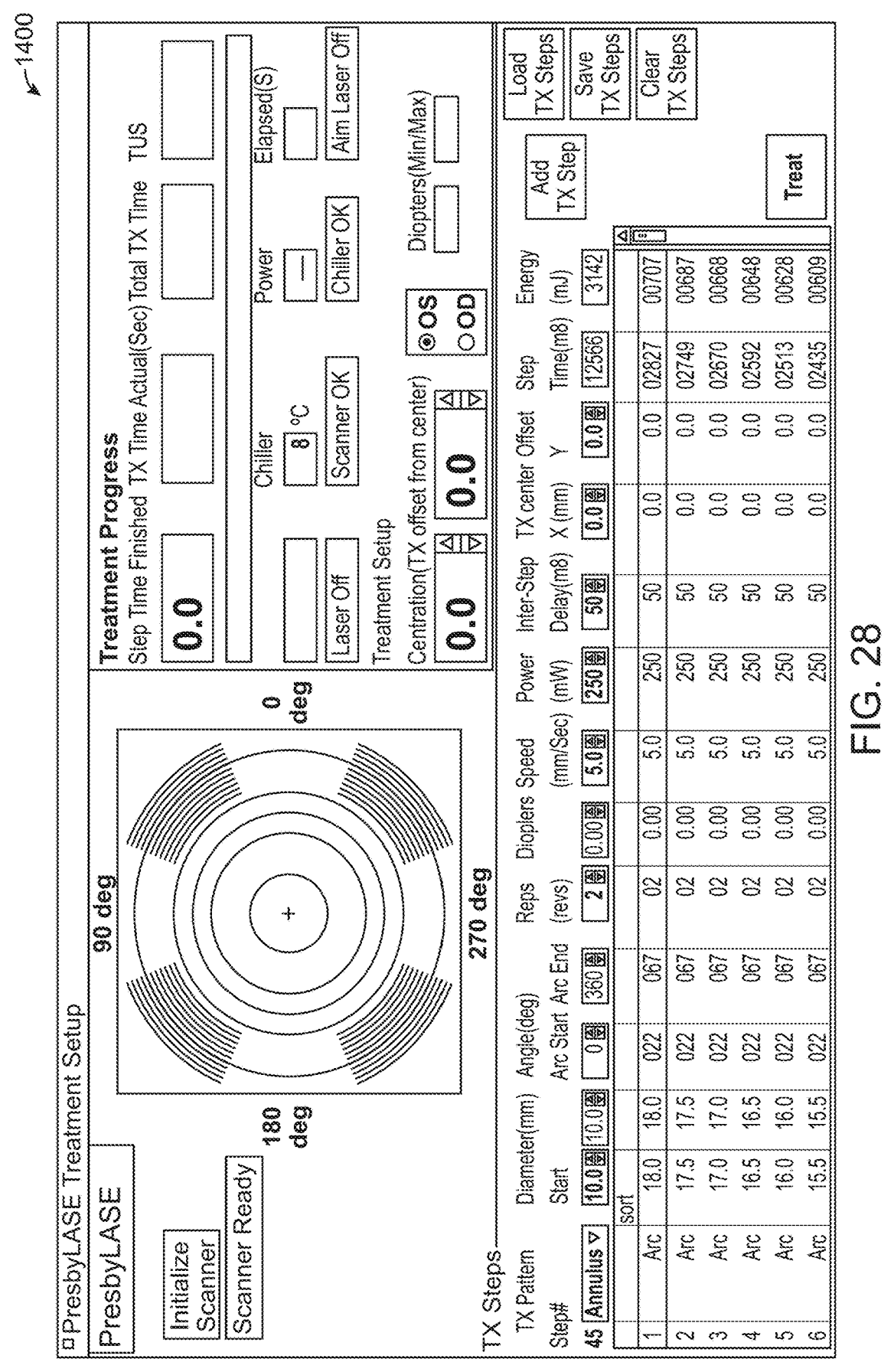

FIG. 28 shows a user interface in accordance with embodiment. The user interface comprises several fields for user's input data and these input fields comprise inputs which can be used to control and configure the laser system. The user interface also includes several outputs and output images which allow the user to confirm that the system is operating correctly. The system comprises a screen, which shows a planned treatment. The screen showing the planned treatment, comprises meridians, such as the 0 degree meridian, the 180 degree meridian, the 90 degree meridian, and the 270 degree meridian. The treatment screen with the planned treatment comprises four quadrants, as described herein.

The user interface comprises several fields for the user to input the scanned treatment. The scanned treatment may comprise a number of treatment steps. The treatment steps may comprise a plurality of treatment patterns. The treatment patterns may comprise, for example, an annulus. The treatment steps may be applied sequentially or together, for example. Each of the treatment steps can be provided with a step number of a treatment table. The treatment table may comprise of plurality of steps, for example, step 1 to step 45, as shown on the display of FIG. 28, step #25 is shown, for example, within the configuration of the input. Step #45 comprises an annulus as shown, the start diameter is at 10 millimeters, which can be varied by user input. There is also an angle that can be offset with an arc start and an arc end. The angle can start at 0 degrees, and end at 360 degrees, for example. Each of the steps can be repeated, with a number of revolutions, for example, two full revolutions of 360 degrees of the treatment pattern with the corresponding area as shown on the image of the treatment pattern, for example.

Alternatively or in combination, refractive treatment can be entered, for example, a refractive treatment in diopters if helpful.

The scan speed can also be set, for example, the scan speed can be set in millimeters per second, in the embodiment shown, the scan speed has been selected to 5 millimeters per second, although the speed can range from any number of values such as a fraction of a millimeter per second, to over a meter per second, for example.

The power of the laser beam is specified in milliwatts, for example, 250 milliwatts, for a continuous wave system. Alternatively, the power can be specified for a post-laser system, and the power can be specified as an energy per pulse, or alternatively, the power can be specified as an energy of the laser beam pulses applied per unit time, alternatively or in combination, the laser beam pulse energy can be specified in the frequency of the laser beam pulses specified in order to define the power of the treatment.

The user interface screen also comprises an inter-step delay which can be applied between each step so as to provide a beneficial result, for example, in order to provide healing and help healing and in order to inhibit damage to the tissue. The inter-step delay can be specified in milliseconds and can be, for example, 50 milliseconds as shown alternatively, the delay can be 1 millisecond, 0 milliseconds, 100 milliseconds, or a second, for example.

The treatment center can be offset. The treatment center offset can be specified in x and y millimeters with a coordinate reference system. Alternatively, the treatment offset can be specified in angular degrees and with a radio component, for example. In the screen shown, the treatment center offset can be specified as an x value in millimeters and a y value in millimeters for example. In which case the x offset would correspond to the 0 and 180 degree meridians as shown, and the y offset to the 90 and 270 degree meridians as shown.

A time of the step can be calculated or input by the user, and the time in milliseconds for example, can be 12,566 milliseconds, which corresponds to approximately 12.5 seconds. The total energy applied can also be provided for the user to provide a beneficial treatment, for example, the total energy of 3,142 millijoules, for example.

As shown in FIG. 28, the image of the treatment plan shown on the display may comprise one or more markers suitable to provide a reference with respect to the eye to be treated. For example, a plurality of concentric rings can be shown, such as the rings are aligned about an axis of the eye for example, an axis, an optical axis of the eye. In many embodiments, the plurality of rings comprises a ring sized to mark the limbus of the eye such that during treatment, the ring can be aligned with the limbus of the eye. In many embodiments, the plurality of rings can be evenly spaced, for example, with increments of 5 millimeter diameter. For example, two rings can be provided inwardly of the limbal marker ring. A first ring at 5 millimeters and a second ring at 10 millimeters. Outward of the marking ring of the limbus, a first ring can be provided at about 15 millimeters and a second ring at about 20 millimeters in diameter. As shown in FIG. 28, the treatment of the scleral tissue outward of the limbus corresponds to treatment aligned with the outer two rings at dimension of approximately 15 millimeters to about 23 millimeters diameter.

The user interface may comprise a treatment status area on the display. The treatment progress can be showed with a step and a time at which the step was finished, for example. A treatment time which is the actual treatment time in seconds, a total treatment time, for example, a chiller temperature, a power temperature, and then elapsed time in the centration can be offset as noted above. The laser system in treatment apparatus as described herein is suitable for combination with one or more of many types of surgery. For example, surgery to treat glaucoma as described herein, such as posterior open angle glaucoma (hereinafter "POAG"), and in many embodiments may be combined with corneal refractive surgery. For example, with reshaping of the stromal tissue of the cornea.

When the desired treatment has been determined, the treatment may be modified, for example, by adding or removing treatment steps with an add treatment step button to provide an even more improved treatment. And additional steps can be added or deleted as appropriate.

When a desired treatment has been verified to be appropriate by the user, the treatment steps can be loaded onto a system controller or alternatively, treatment can be saved with the save treatment steps button, or alternatively the planned treatment can be removed from the screen with the clear treatment steps.

Figure 29:
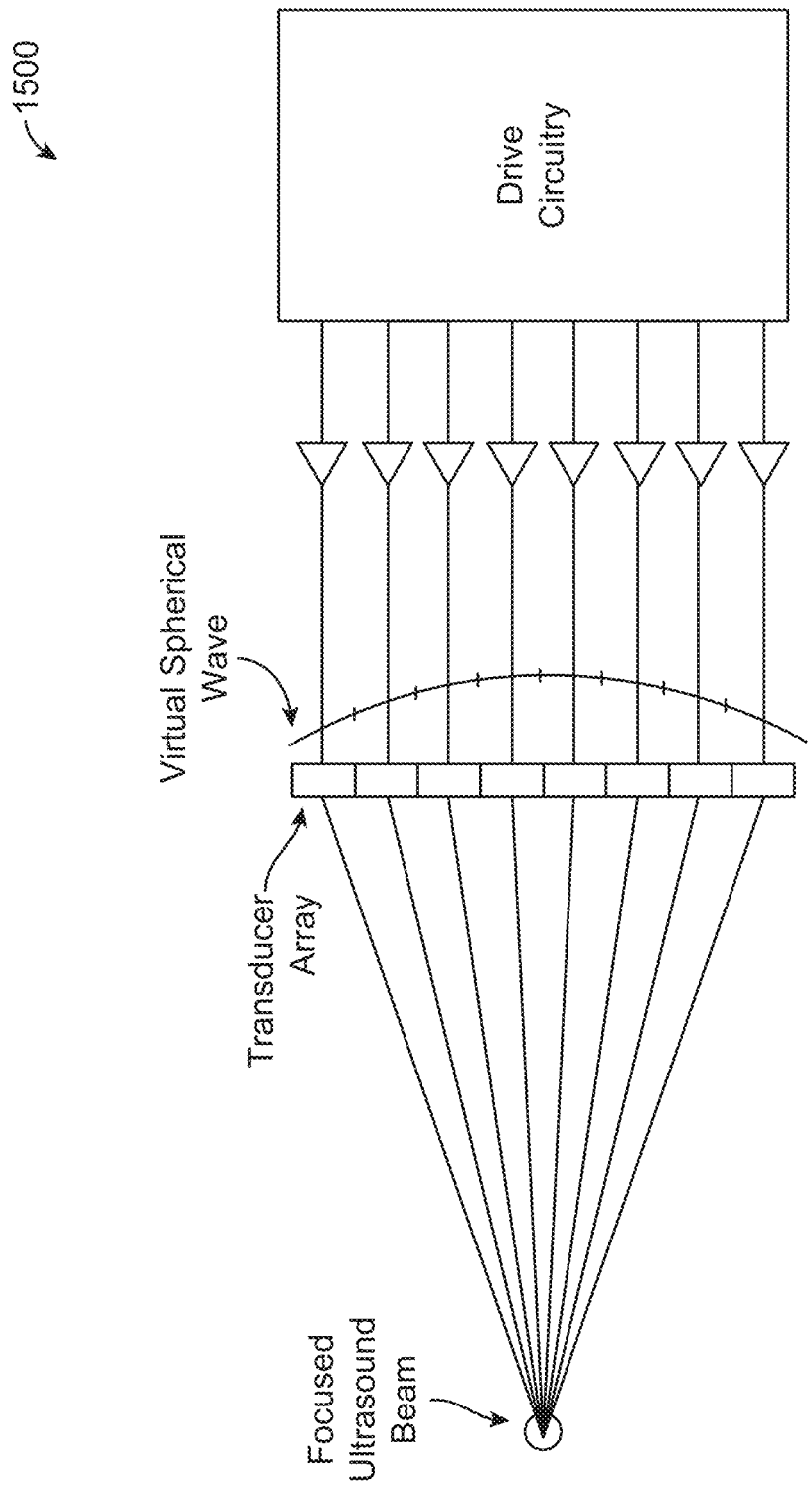
FIG. 29 shows array ultrasound transmitter array to treat tissue, in accordance with embodiments.

FIG. 29 shows array ultrasound transducer array circuitry 1500 to treat tissue. The ultrasound circuitry may comprise one or more components of the treatment apparatus as described herein. The transducer array can be configured to treat the eye in a manner similar to the light energy as described herein, in order to treat one or more of presbyopia or glaucoma.

The transducer array can be configured to treat tissue near the surface of the eye and provide a treatment profile as described herein. Alternatively or in combination, the circuitry can be configured to treat the eye beneath the sclera.

In many embodiments, the transducer array is configured to treat the posterior vitreous zonule in order to increase accommodation. The transducer array can be configured with a time and corresponding phase delay so as to provide a spherical ultrasound wave directed toward the targeted tissue. The transducer array can be configured such that a virtual spherical wave corresponding to time variations and phase variations of the transducer array is provided. The circuitry of the ultrasound system can be configured to provide the focused ultrasound beam to focus energy on the posterior vitreous zonules, for example.

In many embodiments, the ultrasound transducer array is configured to treat a posterior vitreous zonule. The circuitry and transducer array, and can be configured to release tension of the posterior vitreous zonule in order to provide increased movement of the lens of the eye. Alternatively or in combination, the transducer array can be configured to ablate the posterior vitreous zonule in order to provide increase accommodative amplitude of the eye. In some embodiments, an ultrashort pulsed laser such as a femto second laser can be used to incise the posterior vitreous zonule in order to increase accommodation.

Alternatively or in combination with treatment, the ultrasound apparatus can be used to image the eye.

The ultrasound transducer array may comprise one or more commercially available components known to a person of ordinary skill in the art, such as components commercially available from Maxim Integrated Circuits, and as described in FIGS. 5 and 6 of the Maxim tutorial 4038 Optimizing Ultrasound-Receiver VGA Output-Referred Noise and Gain: Improves Doppler Dynamic Range and Sensitivity, available on the World Wide Web at maximintegrated.com, for example.

FIGS. 30A to 30D show ultrasound bio-microscopy (hereinafter "UBM") of eyes in accordance with embodiments.

Figure 30A:
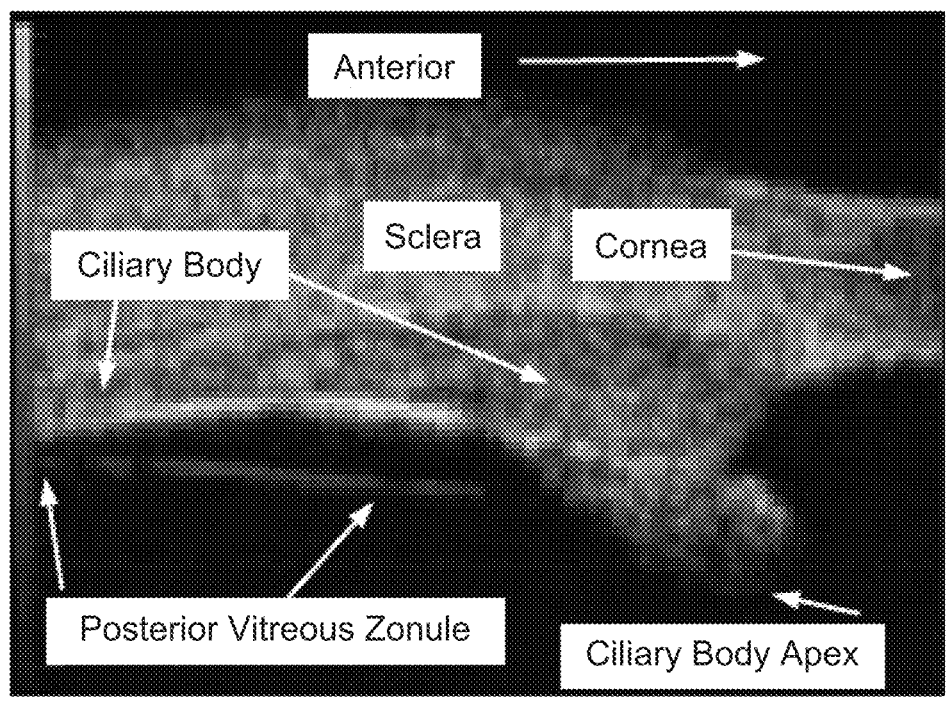
FIG. 30A shows a presbyopic eye in unaccommodated state in accordance with embodiments.

FIG. 30A shows a non-presbyopic eye in unaccommodated state in accordance with embodiments. In the unaccommodated state, the posterior vitreous zonule can be seen in the image shown, and the posterior vitreous zonule extends from an insertion at the ora serrata posteriorly to an anterior insertion near the apex of the ciliary body. In many embodiments, the posterior vitreous zonule is connected to the tissue of the ciliary body at the ora serrata, and the ciliary body can be seen to be moved anteriorly when the eye accommodates.

Figure 30B:
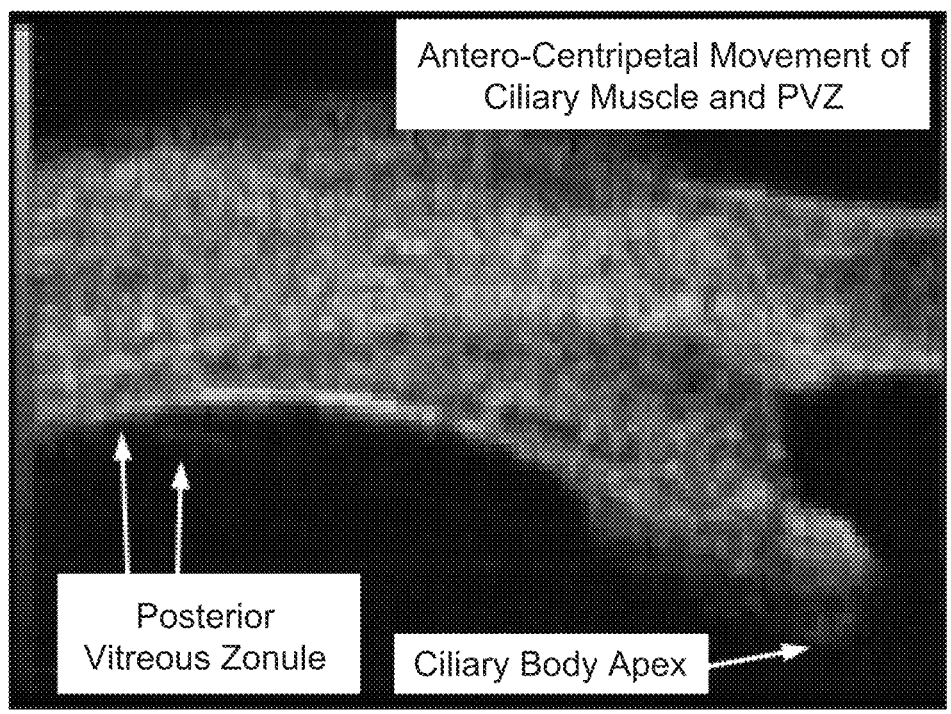
FIG. 30B shows an eye as in FIG. 30A and in an accommodated state.

FIG. 30B shows a non-presbyopic eye as in FIG. 30A in an accommodated state. The ciliary body can be seen to move anteriorly and inward with respect to the ciliary body as shown in FIG. 30A. In addition, the posterior vitreous zonule can be seen to move anteriorly on the eye. This anterior movement of the posterior vitreous zonule at the insertion into the ora serrata allows accommodation. The posterior vitreous zonule may comprise some substantially fixed length with the eye accommodates. In many embodiments, the posterior portion of the posterior vitreous zonule is connected to the ciliary body near a posterior most portion of the ciliary body. The ciliary body where the posterior vitreous zonule connects can be seen to slide anteriorly in order to allow movement of the lens of the eye during accommodation. For example, when the posterior vitreous zonule comprises a substantially fixed length.

The above described images and model and corresponding model can be used to provide improved treatments for accommodation in accordance with embodiments disclosed herein. For example, the softening of the eye can be provided in order to allow anterior and inward movement of the ciliary body, and anterior movement of the posterior vitreous zonule. For example, the scleral tissue between the ora serrata and the apex of the ciliary body can be softened in order to allow movement of the posterior vitreous zonule and ciliary body anteriorly. Alternatively or in combination, in some embodiment, the posterior vitreous zonule can be treated in order to allow the posterior vitreous zonule to stretch.

Figure 30C:
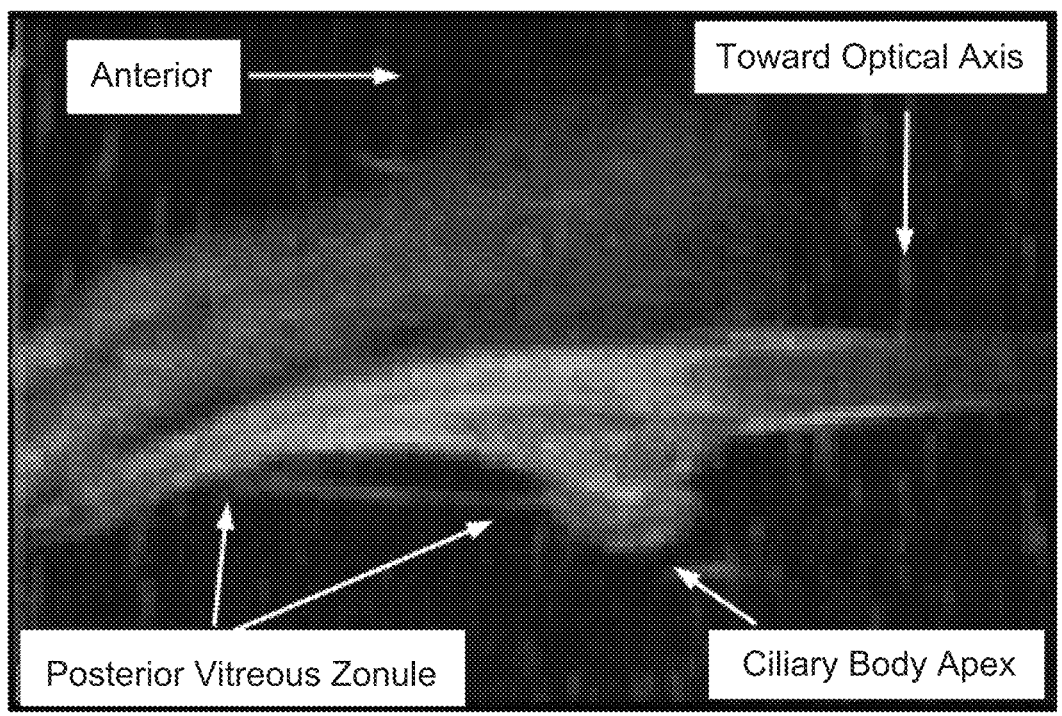
FIG. 30C shows a presbyopic eye suitable for treatment in an unaccommodated state in accordance with embodiments.

FIG. 30C shows a presbyopic eye in an unaccommodated state in accordance with embodiment. The posterior vitreous zonule can be seen to move anteriorly when the eye accommodates. However, the posterior vitreous zonule and corresponding ciliary body tissues do not move as far anteriorly.

Figure 30D:
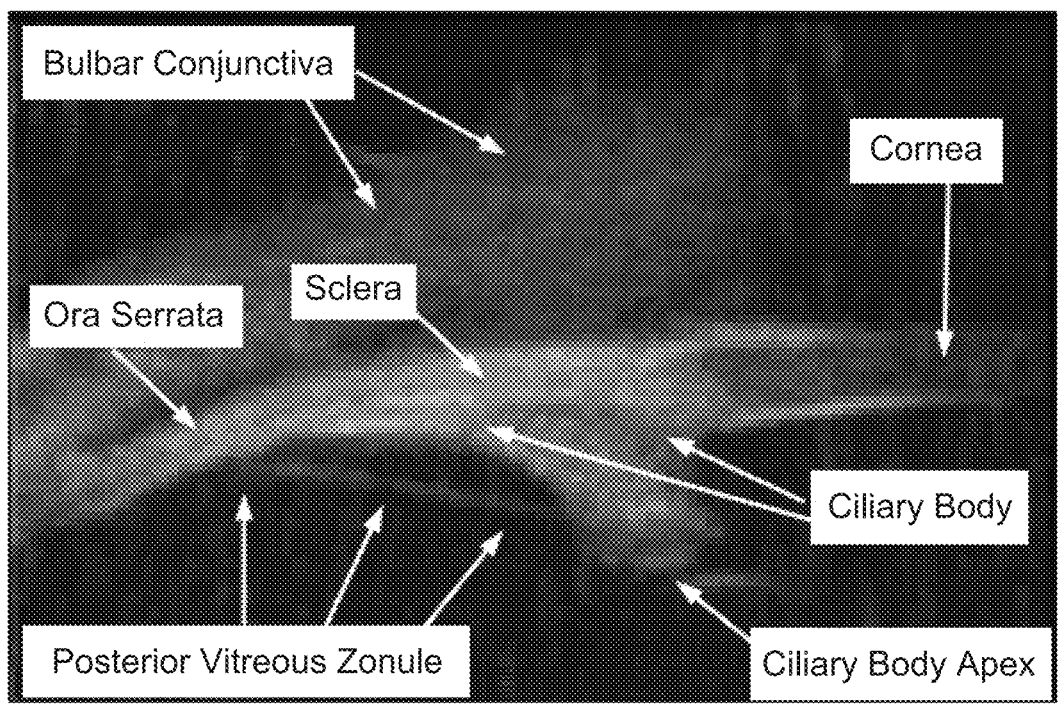
FIG. 30D shows a presbyopic eye suitable for treatment in an accommodated state in accordance with embodiment.

FIG. 30D shows a presbyopic eye in an accommodated state in accordance with embodiment. In the accommodated state the presbyopic eye, the anterior movement of the posterior vitreous zonule is inhibited with respect to the non-presbyopic eye with reference to FIG. 30D, a person of ordinary skill in the art will recognize the movement interiorly of the posterior vitreous zonule is inhibited. In addition, movement of the ciliary body inward to provide accommodation is also inhibited.

The treatments as disclosed herein are well suited to provide a treatment of a presbyopic eye with decreased accommodation as in FIGS. 30C and 30D, and provide improved accommodation with movement of the eye having similarity to the accommodative movement of the eye shown in FIGS. 30A and 30B. For example, the scleral softening, the profile changes and softening of the posterior vitreous zonule may comprise components of the treatment, either alone or in combination as disclosed herein.

Experimental Studies

In accordance with embodiments described herein, a person of ordinary skill in the art can conduct experiments to determine methods, treatments parameters and system configurations to treat presbyopia.

Eyes can be treated in accordance with embodiments disclosed herein, such as treatment energies and times to provide treatment profiles in accordance with embodiments disclosed herein.

In the presbyopic eye, the sclera may bow inward in the region of the scleral spur thereby changing the inner contour of the muscle/zonule complex and the circumlental space is reduced, such that the presbyopic eye may be suitable for treatment in accordance with embodiments. The amount of circumlental space can be directly correlated with accommodative amplitude. In many embodiments shrinking and strengthening the sclera in the region of the lens equator plane restores the sclera/muscle geometry and restore the circumlental space in the aged eye in order to increase accommodation and treat glaucoma, in accordance with embodiments disclosed herein. Modification of the ocular geometry toward that of the young eye can restore some accommodative amplitude, in accordance with embodiments.

Magnetic resonance imaging (MRI) studies can be conducted on eyes in accordance with the studies of Strenk and colleagues, in order to assess the amount of accommodation provided with the STEM procedure as disclosed herein.

The magnetic resonance imaging (MRI) studies of Strenk and colleagues and the Modified Geometric Theory (MGT) of presbyopia development are suitable for incorporation in accordance with embodiments, can be used to determine suitable treatment parameters and can be used to determine treatment parameters in accordance with the mechanism of presbyopia and these MRI findings.

MRI has the ability to provide unique biometric information from the intact human eye during accommodation and with accommodation at rest. These images of the anterior segment can be free of optical or acoustic distortions. Additionally, MRI can acquire sets of images in any desired plane or planes. MRI also offers soft tissue contrast. Also, MRI allows visualization of structures normally hidden by the iris. Ciliary muscle contraction is essentially undiminished throughout life for both phakic and pseudophakic eyes. A changing geometric relationship between the accommodative structures and lifelong lens growth appear to cause an upward and inward ciliary muscle displacement. This results in decreased circumlental space, in many embodiments concomitant with decreased zonular tension, and increased stresses throughout the uveal tissue. In many embodiments, the crystalline lens cross-sectional area is reduced during relaxed accommodation when zonular tension is greatest and the lens material can be slightly compressed. The Modified Geometric Theory (hereinafter "MGT") of Strenk and colleagues can be incorporated in accordance with embodiments disclosed herein. In accordance with embodiments disclosed herein the MGT, lens hardening is not the cause of presbyopia, and lens hardening that occurs with age can be an effect of presbyopia. In accordance with embodiments, the MGT attributes presbyopia to the changing geometric relationship between the ciliary muscle, the zonular apparatus, and the lens. This changing geometry is brought about by lifelong lens growth that results in ciliary muscle displacement and reduced circumlental space, suitable for treatment in accordance with embodiments disclosed herein. With advancing age and decreasing circumlental space, ciliary muscle contraction is undiminished but produces diminishing changes zonular tension, and diminishing changes in lens curvature.

Embodiments disclosed herein are suitable for combination with cataract surgery in order to further lower TOP and increase accommodation, for example. Removing the age-enlarged lens allows the ciliary muscle to return to a more youthful antero-posterior location, and provides opening the drainage angle. In accordance with embodiments, cataract surgery can remove stresses throughout the uveal tissue by facilitating a reduction in the choroidal perimeter after the age-enlarged crystalline lens is removed, and the embodiments disclosed herein are suitable for combination with cataract surgery.

The ciliary muscle can remain active throughout life and lens hardening may not be the cause of presbyopia. Many treatments as described herein alter the geometry between the ciliary muscle, zonular apparatus and lens, and can affect the crystalline lens response to accommodative effort, in order to provide increased accommodation. The STEM procedure as disclosed herein increases the circumlental space within a range from about 200 to 800 microns, for example about 400 microns. MRI studies have demonstrated a significant age-related decrease in circumlental space (approximately 470 microns both nasally and temporally over the adult lifespan), and the increased circumlental space produced by the STEM procedure as disclosed herein can provide a mechanism for the improvement in near vision. Changes in the geometric relationship of the accommodative structures may also lead to a reduction in TOP when the drainage angle is increased or when tension of the uvea decreases, for example. Such changes may with the STEM procedure.

Examples of suitable studies that can be performed by a person of ordinary skill in the art in order to determine the efficacy of the STEM procedure in accordance with embodiments as disclosed herein are described in the following publications, which are incorporated by reference in their entirety to the maximum extent permitted by applicable law and treaties:

Strenk S A, Semmlow J L, Strenk L M, Munoz P, Gronlund-Jacob J, DeMarco J K. Age-related changes in human ciliary muscle and lens: a magnetic resonance imaging study. Invest Ophthalmol Vis Sci 1999; 40:1162-1169.

Strenk S A, Strenk L M, Guo S. Magnetic resonance imaging of aging, accommodating, phakic, and pseudophakic ciliary muscle diameters. J Cataract Refract Surg 2006; 32:1792-1798.

Strenk S A, Strenk L M, Semmlow J L. High resolution MRI study of circumlental space in the aging eye. J Refract Surg 2000; 16:5659-660.

Strenk S A, Strenk L M, Koretz J F. The mechanism of presbyopia. Prog Retin Eye Res 2005; 24:379-393.

Strenk S A, Strenk L M, Guo S. Magnetic resonance imaging of the anteroposterior position and thickness of the aging, accommodating, phakic, and pseudophakic ciliary muscle. J Cataract Refract Surg 2010; 36:235-241.

Poley B J, Lindstrom R L, Samuelson T W. Long-term effects of phacoemulsification with intraocular lens implantation in normotensive and ocular hypertensive eyes. J Cataract Refract Surg 2008; 34:735-742.

Poley B J, Lindstrom R L, Samuelson T W, Schulze Jr R. Intraocular pressure reduction after phacoemulsification with intraocular lens implantation in glaucomatous and nonglaucomatous eyes. Evaluation of a causal relationship between the natural lens and open-angle glaucoma. Journal of Cataract and Refractive Surgery 2009; 35:1946-1955.

While preferred embodiments of the present disclosure have been shown and described herein, it will be obvious to those skilled in the art that such embodiments are provided by way of example only. Numerous variations, changes, and substitutions will be apparent to those skilled in the art without departing from the scope of the present disclosure. It should be understood that various alternatives to the embodiments of the present disclosure described herein may be employed without departing from the scope of the present invention. Therefore, the scope of the present invention shall be defined solely by the scope of the appended claims and the equivalents thereof

What is claimed is:

1. An apparatus to treat an eye, the apparatus comprising:
a source of energy to soften a sclera of the eye;
a processor comprising instructions to treat the eye with the source of energy in order to soften the sclera between a lens equator and an insertion of posterior zonule into an ora serrata of the eye, wherein the processor comprises instructions to treat the eye with the source of energy to increase a circumlental space of the eye; and
a cooling structure to contact an outer surface of the eye, wherein the processor comprises instructions to treat the eye with the source of energy when the cooling structure contacts the outer surface of the eye, wherein the cooling structure is shaped to contact a conjunctiva of the eye.

2. An apparatus as in claim 1, wherein the processor comprises instructions to treat the eye with the source of energy to increase movement of a posterior vitreous zonule when the eye accommodates.

3. An apparatus as in claim 1, wherein the cooling structure comprises one or more of a heat sink or a chiller.

4. An apparatus as in claim 3, wherein the cooling structure comprises the heat sink coupled to the chiller, the heat sink comprising a surface to contact the eye and conduct heat from the eye, the chiller comprising a substance having a temperature less than about 20 degrees Celsius and greater than a freezing temperature of saline, wherein the substance comprises a fluid and a fluidic channel extends from the heat sink to the chiller to cycle the fluid through the heat sink and the chiller.

5. An apparatus as in claim 1, wherein the cooling structure comprises a material transmissive to energy of the source.

6. An apparatus as in claim 1, wherein the source of energy comprises a laser beam and the cooling structure comprises a material transmissive to the laser beam.

7. An apparatus as in claim 1, wherein the source of energy comprises a laser beam and the cooling structure comprises a material transmissive to the laser beam and wherein the material comprises ZnSe and the laser beam comprises a wavelength within a range from about 5.8 to about 6.6 um.

8. An apparatus as in claim 7, wherein the laser beam is configured to have a greater absorbance by stroma than by water.

9. An apparatus as in claim 1, wherein the processor comprises instructions to treat the eye such that vitreous zonules at the ora serrata move at least anteriorly when the eye accommodates at least about one diopter.

10. An apparatus as in claim 1, wherein the processor comprises instructions to treat the eye such that vitreous zonules at the ora serrata move at least anteriorly at least about 1 mm when the eye accommodates at least about one diopter and softened scleral tissue moves interiorly toward an optical axis of the eye.

11. An apparatus as in claim 1, wherein the processor comprises instructions to treat the eye such that an apex of a ciliary body is translocated away from an optical axis of the eye to increase the circumlental space of the eye.

12. An apparatus as in claim 1, wherein the processor comprises instructions to treat the eye such that energy is transmitted through the conjunctiva of the eye to soften the sclera.

13. An apparatus as in claim 1, wherein the processor comprises instructions to treat the eye such that the conjunctiva of the eye comprises at least one layer of viable cells under a location of the conjunctiva irradiated with the source of energy and a heated region comprising softened scleral tissue.

14. An apparatus as in claim 1, wherein the processor comprises instructions to treat the eye such that the conjunctiva of the eye is cooled to a peak temperature less than a peak temperature of the sclera.

15. An apparatus as in claim 14, wherein the processor comprises instructions to treat the eye such that an outer epithelial layer of the conjunctiva is heated to a temperature of no more than about 43 degrees Celsius and a portion of a scleral stroma is heated to at least about 50 degrees Celsius to soften the scleral stroma.

16. An apparatus as in claim 1, wherein the processor comprises instructions to treat the eye such that at least about half of an electromagnetic light energy from the source of energy is absorbed with the conjunctiva of the eye and wherein a scleral stroma of the eye is heated more than the conjunctiva of the eye.

17. An apparatus as in claim 1, wherein the processor comprises instructions to treat the eye such that the conjunctiva of the eye is incised in order to treat the sclera.

* * * * *